US012672850B2

(12) United States Patent
Pang et al.

(10) Patent No.: US 12,672,850 B2
(45) Date of Patent: Jul. 7, 2026

(54) PLANAR LINEAR ARRAY FOR ULTRASOUND

(71) Applicant: FUJIFILM SonoSite, Inc., Bothell, WA (US)

(72) Inventors: Guofeng Pang, Bothell, WA (US); Oleg Ivanytskyy, Bothell, WA (US); Robert Kolaja, Bothell, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 89 days.

(21) Appl. No.: 18/477,127

(22) Filed: Sep. 28, 2023

(65) Prior Publication Data

US 2024/0050068 A1 Feb. 15, 2024

Related U.S. Application Data

(63) Continuation-in-part of application No. 18/158,904, filed on Jan. 24, 2023.
(Continued)

(51) Int. Cl.
*A61B 8/00* (2006.01)
*B06B 1/06* (2006.01)
(Continued)

(52) U.S. Cl.
CPC ............ *A61B 8/4488* (2013.01); *B06B 1/067* (2013.01); *H10N 30/072* (2023.02); *H10N 30/88* (2023.02); *B06B 2201/76* (2013.01)

(58) Field of Classification Search
CPC ..... A61B 8/4488; A61B 8/4483; B06B 1/067; B06B 2201/76; B06B 1/0622;
(Continued)

(56) References Cited

U.S. PATENT DOCUMENTS 10,596,597 B2 3/2020 Chaggares et al.
11,813,640 B2 11/2023 Pang et al.
(Continued)

FOREIGN PATENT DOCUMENTS

KR 101625657 B1 * 5/2016 ........... A61B 8/4444

OTHER PUBLICATIONS

Search Report received in related International Application No. PCT/US2024/049091, mailed Dec. 6, 2024, 19 pages.
(Continued)

*Primary Examiner* — Kaitlyn E Sebastian
(74) *Attorney, Agent, or Firm* — Womble Bond Dickinson (US) LLP

(57) ABSTRACT

Examples herein include piezoelectric layers of an ultrasound transducer, ultrasound transducers, methods of manufacturing the transducers, and methods of manufacturing the piezoelectric layers of an ultrasound transducer. In one example, a piezoelectric layer of an ultrasound transducer include a non-metallic frame and a piezoelectric material. The non-metallic frame surrounds the piezoelectric material on at least two sides and is coupled to a lens support structure with a structure such that an acoustic lens and the piezoelectric material are oriented substantially parallel to each other. The piezoelectric material is sized to span an area greater than or equal to an active surface of the acoustic lens.

22 Claims, 27 Drawing Sheets

Related U.S. Application Data

(60) Provisional application No. 63/368,756, filed on Jul. 18, 2022.

(51) Int. Cl.
    *H10N 30/072*        (2023.01)
    *H10N 30/88*         (2023.01)

(58) Field of Classification Search
    CPC .... B06B 1/0207; H10N 30/072; H10N 30/88; H10N 30/02; G10K 11/30
    See application file for complete search history.

(56) References Cited

U.S. PATENT DOCUMENTS

| | | | |
|---|---|---|---|
| 2005/0165313 A1 | 7/2005 | Byron et al. | |
| 2014/0211587 A1* | 7/2014 | Kiyose | G01S 7/52053 |
| | | | 367/87 |
| 2014/0350407 A1 | 11/2014 | Chaggares et al. | |
| 2017/0144192 A1 | 5/2017 | Chaggares et al. | |
| 2017/0188995 A1 | 7/2017 | Bruestle et al. | |
| 2019/0200959 A1* | 7/2019 | Chaggares | A61B 8/4483 |
| 2020/0196992 A1 | 6/2020 | Li et al. | |
| 2021/0094071 A1* | 4/2021 | Yamada | G01S 7/521 |
| 2021/0121159 A1 | 4/2021 | Bertocci et al. | |
| 2021/0146403 A1* | 5/2021 | Pang | G10K 11/346 |

OTHER PUBLICATIONS

International Preliminary Report on Patentability received for PCT application No. PCT/US23/70363, mailed on Jan. 30, 2025, 8 pages.

International Search Report and Written Opinion for International Patent Application No. PCT/US2023/070363, mailed Oct. 9, 2023, 14 pages.

Ex Parte Quayle Action received for U.S. Appl. No. 18/158,904, mailed on Mar. 19, 2026, 7 pages.

Notice of Allowance received for U.S. Appl. No. 18/158,904, mailed on May 5, 2026, 7 pages.

International Preliminary Report on Patentability received for PCT Patent Application No. PCT/US2024/049091, mailed on Apr. 9, 2026, 13 pages.

\* cited by examiner

100

310

420

725

800

900

1800

2045

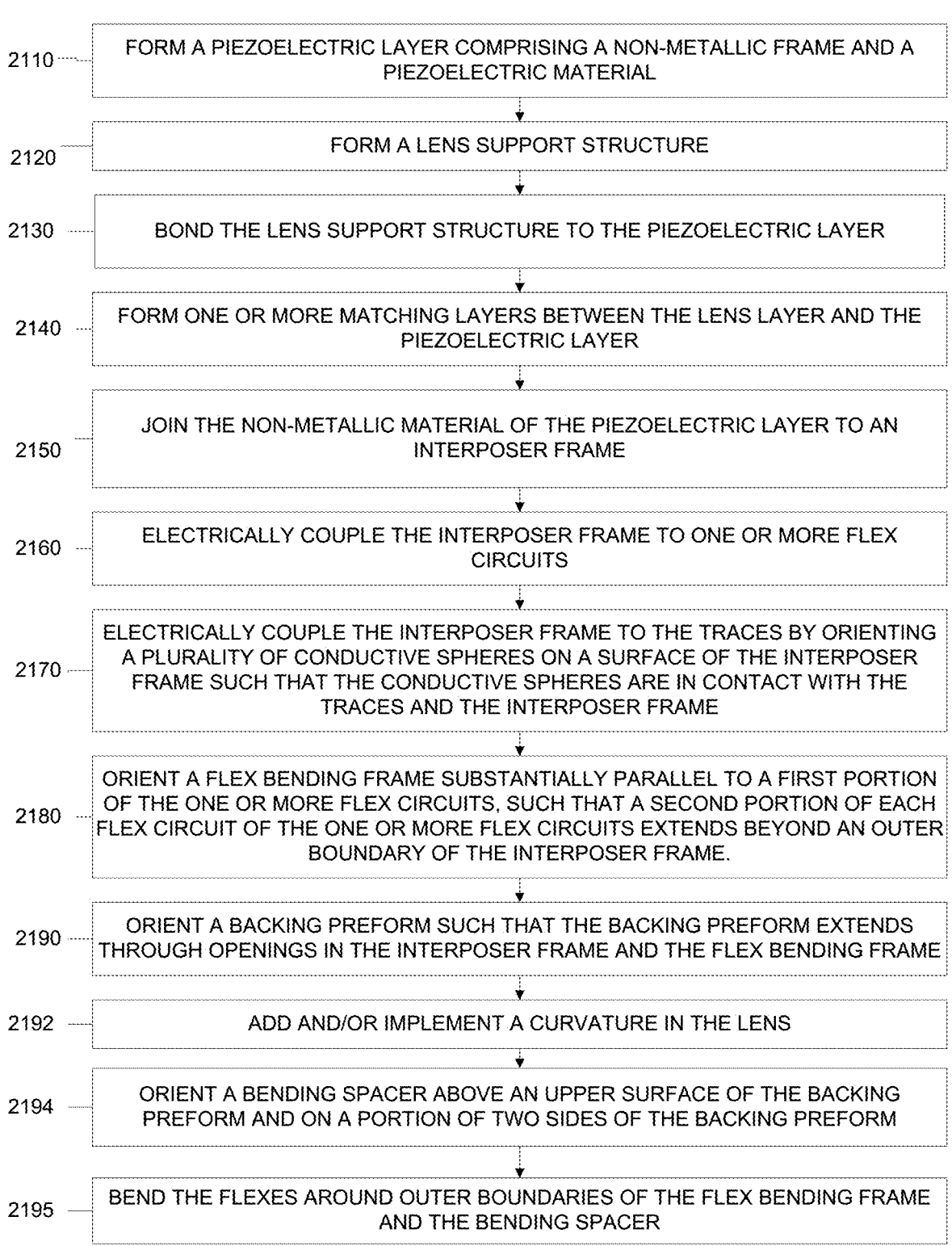

2100

2110 ···· FORM A PIEZOELECTRIC LAYER COMPRISING A NON-METALLIC FRAME AND A PIEZOELECTRIC MATERIAL

2120 ···· FORM A LENS SUPPORT STRUCTURE

2130 ···· BOND THE LENS SUPPORT STRUCTURE TO THE PIEZOELECTRIC LAYER

2140 ···· FORM ONE OR MORE MATCHING LAYERS BETWEEN THE LENS LAYER AND THE PIEZOELECTRIC LAYER

2150 ···· JOIN THE NON-METALLIC MATERIAL OF THE PIEZOELECTRIC LAYER TO AN INTERPOSER FRAME

2160 ···· ELECTRICALLY COUPLE THE INTERPOSER FRAME TO ONE OR MORE FLEX CIRCUITS

2170 ···· ELECTRICALLY COUPLE THE INTERPOSER FRAME TO THE TRACES BY ORIENTING A PLURALITY OF CONDUCTIVE SPHERES ON A SURFACE OF THE INTERPOSER FRAME SUCH THAT THE CONDUCTIVE SPHERES ARE IN CONTACT WITH THE TRACES AND THE INTERPOSER FRAME

2180 ···· ORIENT A FLEX BENDING FRAME SUBSTANTIALLY PARALLEL TO A FIRST PORTION OF THE ONE OR MORE FLEX CIRCUITS, SUCH THAT A SECOND PORTION OF EACH FLEX CIRCUIT OF THE ONE OR MORE FLEX CIRCUITS EXTENDS BEYOND AN OUTER BOUNDARY OF THE INTERPOSER FRAME.

2190 ···· ORIENT A BACKING PREFORM SUCH THAT THE BACKING PREFORM EXTENDS THROUGH OPENINGS IN THE INTERPOSER FRAME AND THE FLEX BENDING FRAME

2192 ···· ADD AND/OR IMPLEMENT A CURVATURE IN THE LENS

2194 ···· ORIENT A BENDING SPACER ABOVE AN UPPER SURFACE OF THE BACKING PREFORM AND ON A PORTION OF TWO SIDES OF THE BACKING PREFORM

2195 ···· BEND THE FLEXES AROUND OUTER BOUNDARIES OF THE FLEX BENDING FRAME AND THE BENDING SPACER

PLANAR LINEAR ARRAY FOR ULTRASOUND

CROSS-REFERENCE TO RELATED APPLICATION

This application claims priority to U.S. patent application Ser. No. 18/158,904, filed Jan. 24, 2023, entitled "PLANAR LINEAR ARRAY FOR ULTRASOUND," which claims priority to U.S. Provisional Application No. 63/368,756 filed Jul. 18, 2022, entitled, "PLANAR LINEAR ARRAY FOR ULTRASOUND" which are both incorporated herein by reference in their entirety, for all purposes.

BACKGROUND

In conventional ultrasound diagnostic imaging systems, arrays are used as an interface to convert electrical signal into ultrasound waves and reconvert the received, reflected ultrasound from a tissue structure to an electrical signal. Certain arrays utilize a fixed acoustic lens, such as a convex RTV (room-temperature-vulcanizing silicone) lens, in the elevation direction to focus the ultrasound beam to improve image resolution or image slice thickness. Currently, the most popular ultrasound transducers in medical imaging are ID arrays, which utilize a fixed aperture with an acoustic lens in the elevation to improve image resolution. Transducer elements can be arranged in a linear 1 D row or chain (a so-called linear array) and can be controlled by an electronic control unit, separately or in groups, to achieve a directing effect. Although the elevational resolution can be improved by using controlled multi-row arrays (e.g., 1.25D or 1.5D) for elevation aperture adjustment, the cost of building multi-row arrays in production is high due to the complicated electrical interconnections among rows and columns. The complexity of these connections also opens possibilities for malfunctions and can affect the longevity of a device. Additionally, although the elevational resolution can be improved, current multi-row arrays introduce a limitation of all rows typically being of the same center frequency.

Certain arrays utilized in connection with ultrasound imaging are free field voltage sensitivity (FFVS) high frequency (HF) arrays and are built on metal tapered support structures. The existing structures used to mount these arrays increase the complexity of the resultant probes, in part because mounting various aspects at an angle proves necessary to the functionality and structural integrity of the array. For example, mounting flex circuits of the array at equal to or approximately a 45-degree angle on this tapered support structure preserves lateral space and creates an electrical path vertically by adding a molded insulation layer. The metal in the tapered support structure lends mechanical strength to the array structure and serves as a ground path. However, the angled nature of the structure, which provides the desired functionality, as aforementioned, renders assembly challenging. Existing ultrasound transducers have complex 3D structures within their array stacks. Assembling these stacks is a lengthy process; the process includes complex tooling by operators with a high level of skill.

SUMMARY

Shortcomings of the prior art can be overcome and benefits as described later in this disclosure can be achieved through the provision of a piezoelectric layer of an ultrasound transducer. Various examples of the piezoelectric layer are described below, and the piezoelectric layer, including and excluding the additional examples enumerated below, in any combination (provided these combinations are not inconsistent), overcome these shortcomings. The piezoelectric layer includes, for instance: a non-metallic frame; and a piezoelectric material, the non-metallic frame surrounding the piezoelectric material on at least two sides, the non-metallic frame coupled to a lens support structure with a structure such that an acoustic lens and the piezoelectric material are oriented substantially parallel to each other, the piezoelectric material sized to span an area greater than or equal to an active surface of the acoustic lens.

Shortcomings of the prior art can be overcome and benefits as described later in this disclosure can be achieved through the provision of a transducer. Various examples of the transducer are described below, and the transducer, including and excluding the additional examples enumerated below, in any combination (provided these combinations are not inconsistent), overcome these shortcomings. The transducer includes, for instance: a planar linear array stack, comprising: a lens layer comprising an acoustic lens and a lens support structure; and a piezoelectric layer comprising: a non-metallic frame; and a piezoelectric material, the non-metallic frame surrounding the piezoelectric material on at least two sides, the non-metallic frame coupled to the lens support structure with a structure such that a portion of the acoustic lens and a portion of the non-metallic frame are oriented substantially parallel to each other, the piezoelectric material sized to span an area greater than or equal to an active surface of the acoustic lens; and the structure to position one or more flex circuits, wherein the one or more flex circuits are coupled to the structure.

Shortcomings of the prior art can be overcome and benefits as described later in this disclosure can be achieved through the provision of an ultrasound transducer. Various examples of the ultrasound transducer are described below, and the ultrasound transducer, including and excluding the additional examples enumerated below, in any combination (provided these combinations are not inconsistent), overcome these shortcomings. The ultrasound transducer includes, for instance: a planar linear array stack, comprising: a lens layer comprising a lens; one or more matching layers between the lens layer and a piezoelectric layer; and a piezoelectric layer comprising: a non-metallic frame; and a piezoelectric material, the non-metallic frame surrounding the piezoelectric material on at least two sides, the non-metallic frame coupled to a portion of the lens support structure with a structure such that an acoustic lens and the non-metallic frame are oriented substantially parallel to each other, the piezoelectric material sized to span an area greater than or equal to an active surface of the acoustic lens; and the structure to position one or more flex circuits, wherein the one or more flex circuits are coupled to the structure.

Shortcomings of the prior art can be overcome and benefits as described later in this disclosure can be achieved through the provision of a method for manufacturing a piezoelectric layer of an ultrasound transducer. Various examples of the method are described below, and the method, including and excluding the additional examples enumerated below, in any combination (provided these combinations are not inconsistent), overcome these shortcomings. The method includes, for instance: dicing piezoelectric material to form a sized piece of piezoelectric material, the dicing including sizing the sized piece of piezoelectric material to span an area equivalent to an active surface of an acoustic lens in the ultrasound transducer;

assembling a four-sided frame from a non-metallic material; forming at least one trench in at least one side of two parallel sides of the four-sided frame; bonding the sized piece of piezoelectric material to the four-sided frame such that the four-sided frame surrounds the sized piezoelectric material on at least two sides; cutting the sized piezoelectric material to form one or more kerfs oriented in a consistent direction; filling the kerfs with a material that cures over a time period; and based on the time period elapsing, sputtering at least the sized piece of piezoelectric material with a conductive material.

Shortcomings of the prior art can be overcome and benefits as described later in this disclosure can be achieved through the provision of a method for manufacturing a transducer. Various examples of the method are described below, and the method, including and excluding the additional examples enumerated below, in any combination (provided these combinations are not inconsistent), overcome these shortcomings. The method includes, for instance: dicing piezoelectric material to form one or more sized pieces of piezoelectric material, wherein the dicing comprises sizing each piece of the one or more sized pieces of piezoelectric material to span at least an area of an active surface of an acoustic lens in an ultrasound transducer; assembling one or more four-sided frames from a non-metallic material; forming at least one trench in each side of two parallel sides of each frame of the one or more four-sided frames four-sided frames; stretching and placing foil over an object comprising a first parallel surface; placing a one or more stencils on a top surface of the foil, wherein each stencil of the one or more stencils comprises an opening to receive and retains in a set position, each sized piece of the one or more sized pieces; utilizing each stencil of the one or more stencils to position a respective sized piece of the one or more sized pieces; bonding each non-metallic frame of the one or more non-metallic frames to a respective sized piece of the one or more sized pieces; and placing a second object comprising a second parallel surface, wherein the first parallel surface and the second parallel surface are parallel to each other, atop the one or more non-metallic frames.

Additional features are realized through the devices and techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

FIG. 21 illustrates a workflow that describes various aspects of some methods of manufacturing the planar linear arrays discussed herein;

DETAILED DESCRIPTION

Figure 1:
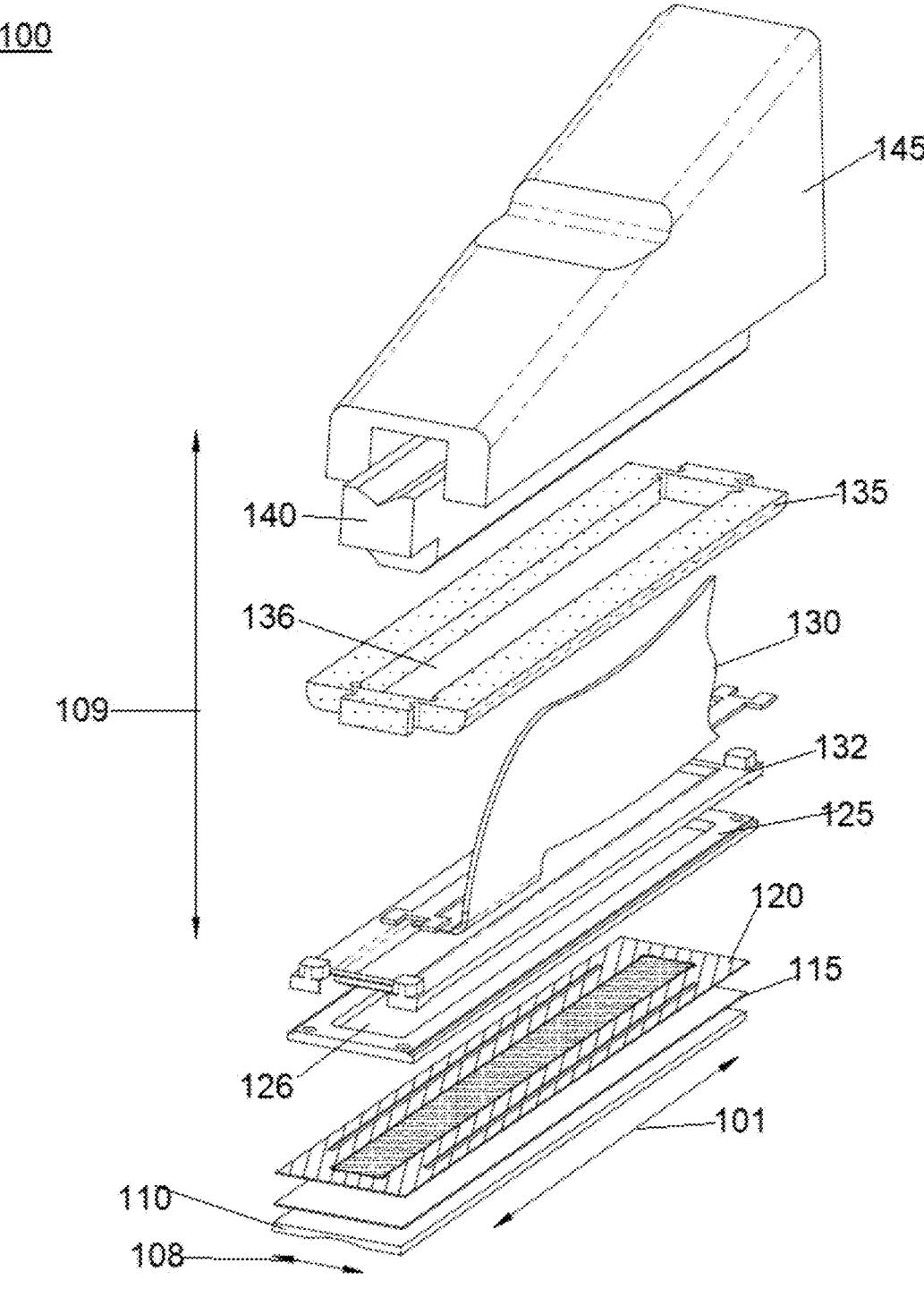
FIG. 1 depicts an exploded view of an example of a planar linear array stack for an ultrasound transducer.

The accompanying figures, which are not drawn to scale for ease of understanding, in which like reference numerals may refer to identical or functionally similar elements throughout the separate views and which are incorporated in and form a part of the specification, further illustrate the present invention and, together with the detailed description of the invention, explain the principles of the present invention. As understood by one of skill in the art, the accompanying figures are provided for ease of understanding and illustrate aspects of certain embodiments of the present invention. The invention is not limited to the embodiments depicted in the figures.

Term Examples

The terms "connect," "connected," "contact" "coupled" and/or the like are broadly defined herein to encompass a variety of divergent arrangements and assembly techniques. These arrangements and techniques include, but are not limited to (1) the direct joining of one component and another component with no intervening components therebetween (i.e., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (notwithstanding the presence of one or more additional components therebetween). It is to be understood that some components that are in direct physical contact with one another may or may not be in electrical contact and/or fluid contact with one another. Moreover, two components that are electrically connected, electrically coupled, optically connected, optically coupled, fluidly connected or fluidly coupled may or may not be in direct physical contact, and one or more other components may be positioned therebetween.

The terms "including" and "comprising", as used herein, mean the same thing.

The terms "substantially", "approximately", "about", "relatively," or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, they can refer to less than or equal to ±10%, such as less than or equal to±5%, such as less than or equal to ±2%, such as less than or equal to ±1%, such as less than or equal to±0.5%, such as less than or equal to±0.2%, such as less than or equal to ±0.1%, such as less than or equal to ±0.05%. If used herein, the terms "substantially", "approximately", "about", "relatively," or other such similar terms may also refer to no fluctuations.

As used herein, "electrically coupled" refers to a transfer of electrical energy between any combination of a power source, an electrode, a conductive surface, a droplet, a conductive trace, wire, waveguide, nanostructures, other circuit segment and the like. The terms electrically coupled may be utilized in connection with direct or indirect connections and may pass through various intermediaries, such as a fluid intermediary, an air gap and the like.

As used herein, the term "kerf" refers to adjustable gaps between diced portions of the acoustic surface that can be filled in each example, with materials that vary (to maintain and adjust the gaps).

The term "ROC" refers to the radius of curvature and is utilized in the context of acoustic design herein. In medical ultrasound arrays, a ROC lens is generally a cylindrical focus lens. The lenses referred to herein as ROC lenses are single radius focus lenses and the lenses referred to herein as multi-ROC lenses are multiple radii focus lenses. An ROC for a convex acoustic lens is a product of the geometric focal length and one less than a result of the speed of sound of the medium divided by the speed of sound of the lens material. Acoustic lenses, which are utilized herein, were designed based on the paraxial theory or Fresnel approximation in geometrical optics, assuming a plane wave front emitted in a direction normal to the transducer surface.

As used herein, the term "PZT" refers to lead zirconate titanate or lead zirconium titanate, which is a ceramic perovskite material that shows a piezoelectric effect, i.e., the compound changes shape when an electric field is applied. In this context, it is utilized in ultrasonic transducers. PZT ceramic is the most commonly used piezoelectric ceramic because it has a greater sensitivity and higher operating temperature than other piezoelectric ceramics. As used herein, the term "SX", which is used in conjunction with "PZT" as "PZT/SX" refers to a single crystal lead zirconate titanate or lead zirconium titanate layer.

As used herein, the term "matching layer" refers to a layer in a transducer array that helps transfer ultrasound energy from the elements to the medium. Matching layers are generally located in examples herein (as well as in existing transducer arrays) between the elements and the lens. Matching layers are comprised of material that are conducive to achieve energy transfer, including but not limited to, epoxy, elastomer, polyurethane, polystyrene, etc. In an ultrasound transducer, one or more matching layers provide an acoustic impedance gradient for the acoustic energy from the transducer to smoothly penetrate the body tissue and for the reflected acoustic waves (the returning echo) to smoothly return to the transducer for detection.

As used herein, the terms "signal flexes" and "ground-return flexes" refer to signal and ground-return elements in flexible electronics, also known as flex circuits, which are circuits that can conform to desired shapes (e.g., flex during use). The term "flex" is a flexible circuit. Flex circuits are utilized as connectors in various applications where flexibility, space savings, and/or production constraints limit the serviceability of rigid circuit boards or hand wiring. Many flexible circuits are passive wiring structures that are used to interconnect electronic components.

As used herein, the term "stack configuration" refers to a pile of objects, referred to herein as "stacks" that, in the context of the examples herein, includes pieces of a piezoelectric layer, diced in elevation into multiple rows, as well as the matching layers and the de-matching layer in some cases. As described herein, each stack configuration is described relative to three dimensions: a width in elevation, a length perpendicular to the width, and a stack-up thicknesses-configuration perpendicular to the length and perpendicular to the width. An example of these dimensions is provided in FIG. 1 herein.

As used herein, the term "beam pattern" (which can also be referred to as an acoustic radiation pattern), is the relative sensitivity of a transducer as a function of spatial angle. This pattern is determined by factors such as the frequency of operation and the size, shape, and acoustic phase characteristics of the vibrating surface. The beam patterns of transducers can be reciprocal, which means that the beam pattern can be the same whether the transducer is used as a transmitter or as a receiver. Generally, transducers can be designed to radiate sound in many different types of patterns having different shapes (e.g., beam widths), from omnidirectional to very narrow beams.

As discussed herein, the term "phased array" (PA) refers to an array of ultrasound transducers that fire individual elements on the array in a specific sequence to direct the sound wave in a specific direction. To that end, a PA probe is comprised of many (e.g., small) ultrasonic transducers, each of which can be pulsed independently. Varying the timing, through this pulsing (e.g., making the pulse from each transducer progressively delayed going up the line), causes the probe to radiate a beam pattern, due to constructive interference, at a set angle, based on the progressive time delay. Changing the progressive time delay can electronically steer the beam.

As used herein, the term "excimer laser", also referred to as a "exciplex laser", is a form of ultraviolet (UV) laser.

As used herein, the term "lens layer" refers to one or more elements in the planar linear array stack described herein that can include an acoustic lens secured to a lens support structure and the lens support structure or, in some examples, the lens layer can include an acoustic lens without a lens support structure.

As used herein, the term "piezoelectric layer" is a layer in a planar linear array stack that can include a piezoelectric material (e.g., PZT, PZT/SX, etc.). As will be discussed in greater detail herein, in some examples, the piezoelectric layer can include a frame which is not comprised of metal (e.g., it can be comprised of ceramic) which frames (e.g., surrounds) a piezoelectric material on at least two sides. This frame is referred to herein as a "non-metallic frame".

As used herein, the term "interposer frame" refers to a structure in a planar linear array stack that is not conductive that can be utilized to position conductive elements, which in the examples herein can include one or more flex circuits. The interposer frame can be comprised of a solid material (e.g., ceramic) with a conductive layer coated on it to bridge out a ground connection and signal electrode connections in the planar linear array stack.

As used herein, the term "overmould" refers to a material that can be utilized in a planar linear array stack to bond and position elements. In the examples herein, the overmould can be utilized to position conductive elements, such as the one or more flex circuits.

As used herein, the term "flex bending frame" is an element of a planar linear array stack that can be used to shape the aforementioned conductive elements positioned by the interposer frame.

As used herein, the term "backing preform" refers to a backing layer in a planar linear array stack that can be utilized to increase the transducer signal quality by absorbing and damping the back-end signal from a ceramic element (e.g., the interposer frame).

As used herein the term "bending spacer" refers to a spacer (spacers can be utilized in transducers to reduce side imaging and interference) which in the examples herein, based on its positioning, can assist in bending conductive elements (e.g., flex circuits).

As used herein, the term "conductive shapes of uniform scale" refers to shapes including, but not limited to spheres, pyramids, and cubes. The term "uniform scale" refers to the shapes having a uniform height (e.g., stack-up thickness). The relative orientation of the height measure will be discussed herein.

As used herein, the term "parallel lap" refers to utilizing a chemical solution, etching gases, or mechanical polish to remove materials layer by layer, including metal and oxide layers. A parallel lapping process can be utilized to remove and/or retain specific layers in a controlled manner.

As used herein, the term "trench" refers, broadly, to any impression made in a material that involves the removal of some of that material. Thus, trenches, herein, can be cutouts, channels, holes, grooves, slots, canals, corrugations, creases, crimps, cuts, etc. Any time a material is removed to create a hole or an impression, regardless of depth, this crevice can be referred to herein as a trench. Additionally, each of the listed terms is used interchangeably to refer to any and all possible types of impressions or holes.

As used herein, the term "bond" used in its various forms as either a noun or a verb refers to the act of affixing an item to another item with a bonding agent, which can include but is not limited to utilizing a bonding agent such as glue and/or epoxy to make this connection. In certain of the examples herein, one can select a bonding agent (creating a bond) based on the bonding agent comprising materials that will not denature due to use of a transducer formed utilizing one or more of the processes described herein.

As used herein in reference to a transducer, the term "high frequency" refers to a transducer that operates with ultrasound above 3 to 5 MHz. Meanwhile, "ultra-high frequency" refers to transducers that operate with ultrasound above IO MHz. The term "low frequency" would refer to a transducer that operates with ultrasound below 3 MHz. These terms are not exact but as will be discussed herein, certain of the examples of the transducers described herein can operate at frequencies that span low to ultra-high.

As used herein the terms "pitch error" and "walk off" both refer interchangeably to unintended geometric changes that occur to various layers, including the piezoelectric layer, during the manufacturing process because of the warping of the layer's dimensions due to the use of heat in the manufacturing process. The functionality of the piezoelectric layer, for example, can be tied to its manufacturing process, including spacing trenches in a consistent manner. In piezoelectric layers, the width of the gaps plus the width of the kerf multiples by the number of kerfs is to equal the length of the piezoelectric, from end to end. Any difference between mathematical and theoretical number that you measure is the pitch error or the walk-off. Some manufacturing processes can add heat to the piezoelectric (e.g., PZT), which is very stressful to the PZT and in some cases, manifests itself as geometry changes and pitch error or walk-off. Piezoelectric layers that are manufactured by utilizing a laser to create ground trenches in piezoelectric material can be particularly susceptible to pitch error or walk off.

As used herein, the term "active surface of the acoustic lens" refers to a portion of a lens that in some of the planar linear arrays described herein is framed in an opening (e.g., a central opening) by a non-metallic frame. The active surface of the acoustic lens is a surface that is covered by a piezoelectric material in a piezoelectric layer described herein. In some literature, the active surface of a transducer refers to piezoelectric material and the "active surface of the acoustic lens" is defined by the location of the piezoelectric material in the stack of a transducer.

As used herein the term "machined" refers to general manufacturing methods which include, but are not limited to conventional machining with an end mill, molding, casting, 3D printing, and any other uses of any machine or implement to create the component described.

As discussed above, some existing arrays utilized in ultrasound transducers are built on metal tapered support structures, which is one example of a complex three-dimensional (3D) structure utilized in this technology. These tapered structures can lend mechanical strength to the array structure, including by preserving lateral space, and can serve as a ground path. However, the result is a complex 3D structure that can be difficult (and expensive) to assemble. Also, the need to angle the flex circuits (e.g., at 45 degrees) can limit the ability to miniaturize the array and thus, render the resultant probe unsuitable for certain applications. Moreover, in a complex 3D structure, it can be challenging to create a flat and parallel surface to a certain tolerance. As the array footprint increases, such as in an ultra-high resolution transrectal ultrasound (UHR-TRUS) probe, it becomes more difficult to maintain flatness to tight tolerances. As the footprint decreases, it is difficult to make tools to handle such a tiny array and to assemble parts onto the tiny array. As will be described below, whether an array comprises the tapered support structure or another existing 3D structure with similar bulk, a need exists to reduce 3D complexity and bulk in transducer arrays. This need is addressed by the examples described herein.

Described herein are a method of manufacturing an ultrasound transducer that includes a planar linear array stack and examples of the transducer comprising this planar linear array stack. Utilizing the transducer with the examples of a planar structure described herein both simplifies the manufacturing process and increases yield without compromising acoustic quality, when compared to existing non-planar examples. Examples of the planar array structure described herein can be integrated into a suitable ultrasound probe, such as an UHR-TRUS probe or a periodontal probe. Various aspects of the examples described herein will be discussed, but certain examples can include: 1) a substantially level (e.g., flat) interposer frame, which can be comprised of a non-metallic material, including but not limited to, ceramic; 2) electrical connections utilizing shapes coated with a conductive material; 3) a piezoelectric frame (also referred to herein as a layer), which is non-conductive (e.g., ceramic) and used to increase mechanical strength, flatten the array to facilitate ease in manufacturing, and provide embedded conductive channels for grounding; 4) a backing preform that fits the planar structure and reduces material costs; 5) a lens layer, which includes a lens with or without a surrounding frame. When present, a lens frame will enhance the mechanical strength and electrical safety isolation. Advantages of the examples of the arrays described herein and the manufacturing process for these examples include but are not limited to simplifying manufacturing tools, eliminating lengthy manufacturing processes, reducing manufacturing difficulties, reducing dependency on operator skills, reducing failure rates, and decreasing reduction costs.

Figure 2:
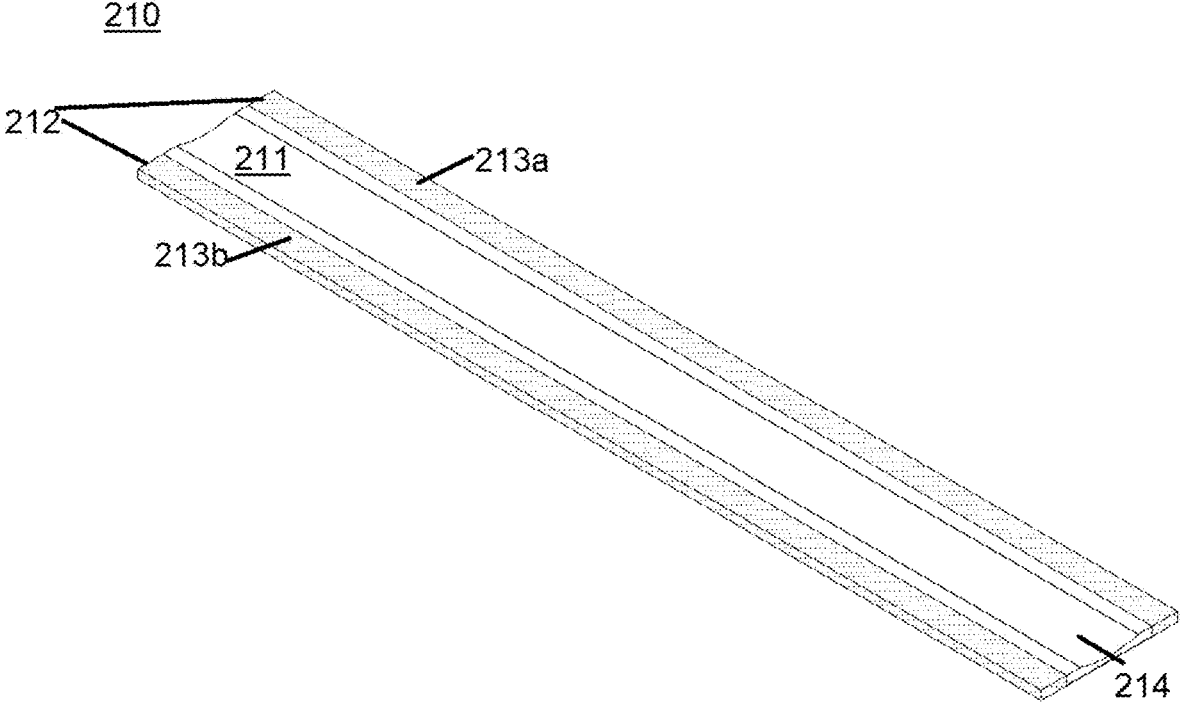
FIGS. 2 and 3 both depict examples of a lens layer which can be integrated into examples of the planar linear array stacks described herein.
Figure 3:
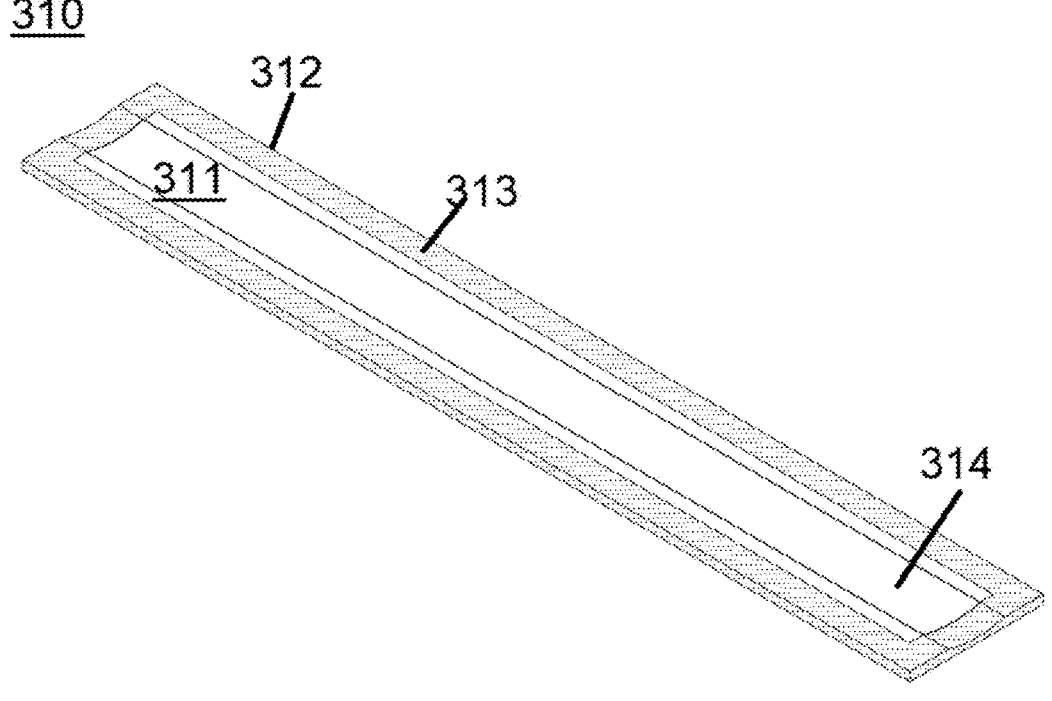
Figure 4:
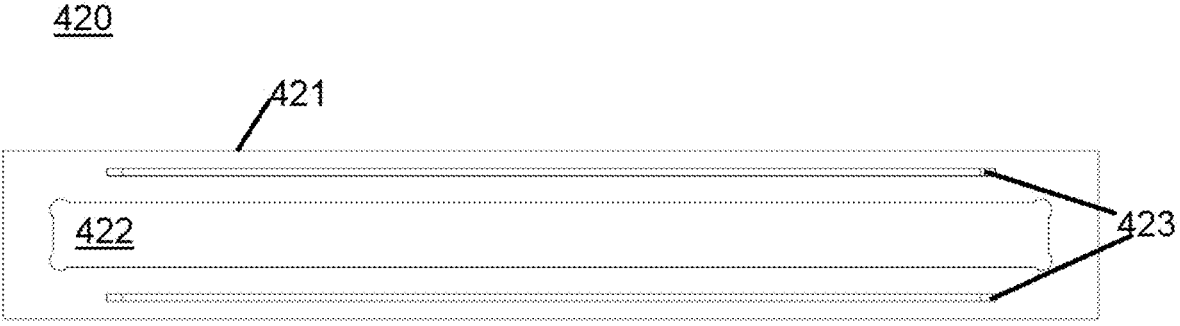
FIG. 4 depicts an example of a piezoelectric layer which can be integrated into examples of the planar linear array stacks described herein.
Figure 5:
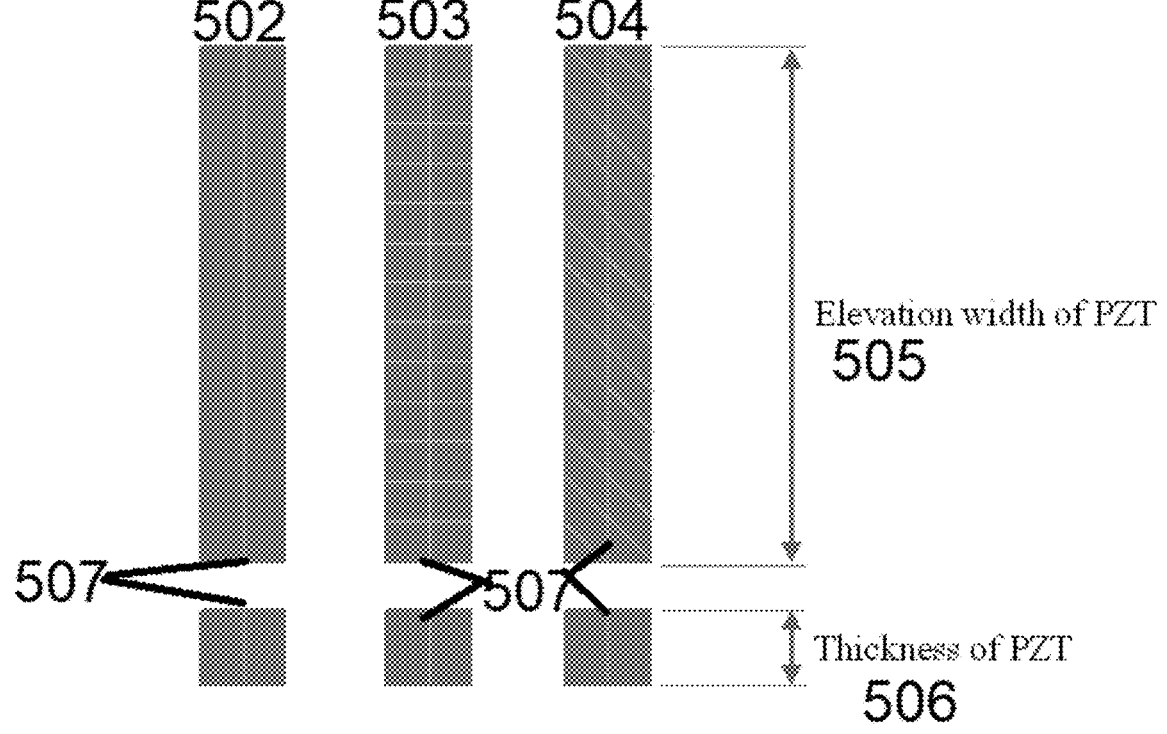
FIG. 5 illustrates different patterns that a laser can be used to form in the piezoelectric material integrated into examples of the planar linear array stacks described herein.

FIG. 1 depicts an exploded view of an example of a planar linear array stack 100 for an ultrasound transducer. In this figure, certain aspects are described in general terms and the figures that follow illustrate, in more detail, these aspects. For instance, FIGS. 2 and 3 illustrate various aspects of a lens layer 210, 310 in a planar linear array stack 100 (FIG. 1). FIG. 4 depicts an upper view of various aspects of a piezoelectric layer 420 in the planar linear array stack 100 (FIG. 1) while FIG. 5 depicts various examples of piezoelectric materials that are part of the piezoelectric layer 120

Figure 6:
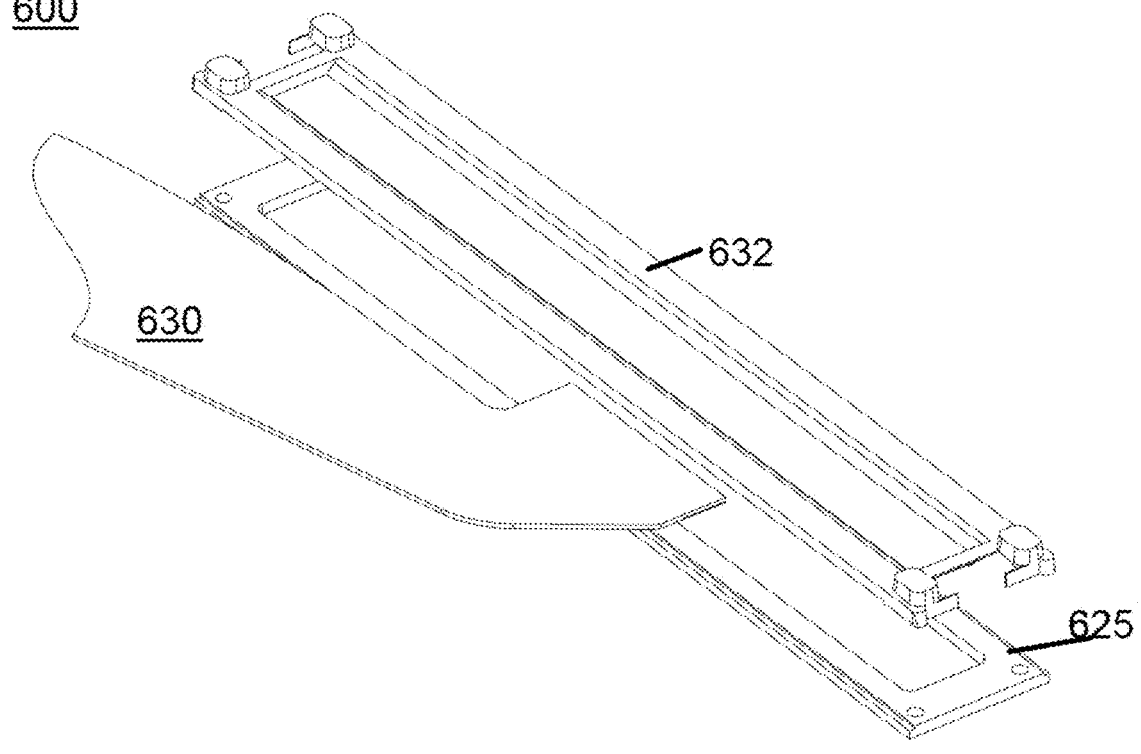
FIG. 6 depicts a structure that can be integrated into examples of the planar linear array stacks described herein that serves to secure flex circuits in the planar linear array stack.
Figure 7:
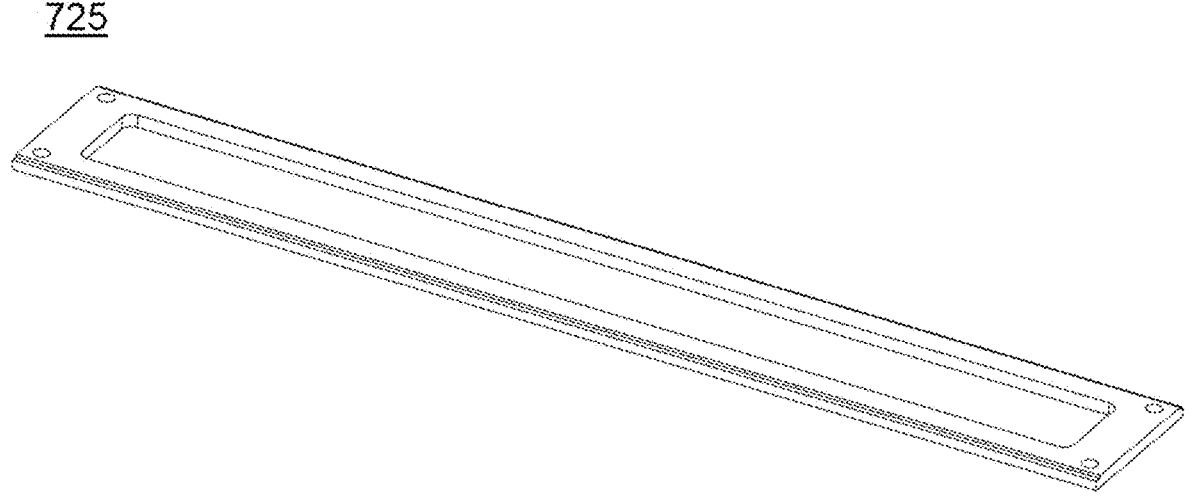
FIG. 7 depicts an example of an interposer frame that can be integrated into examples of the planar linear array stacks described herein.
Figure 8:
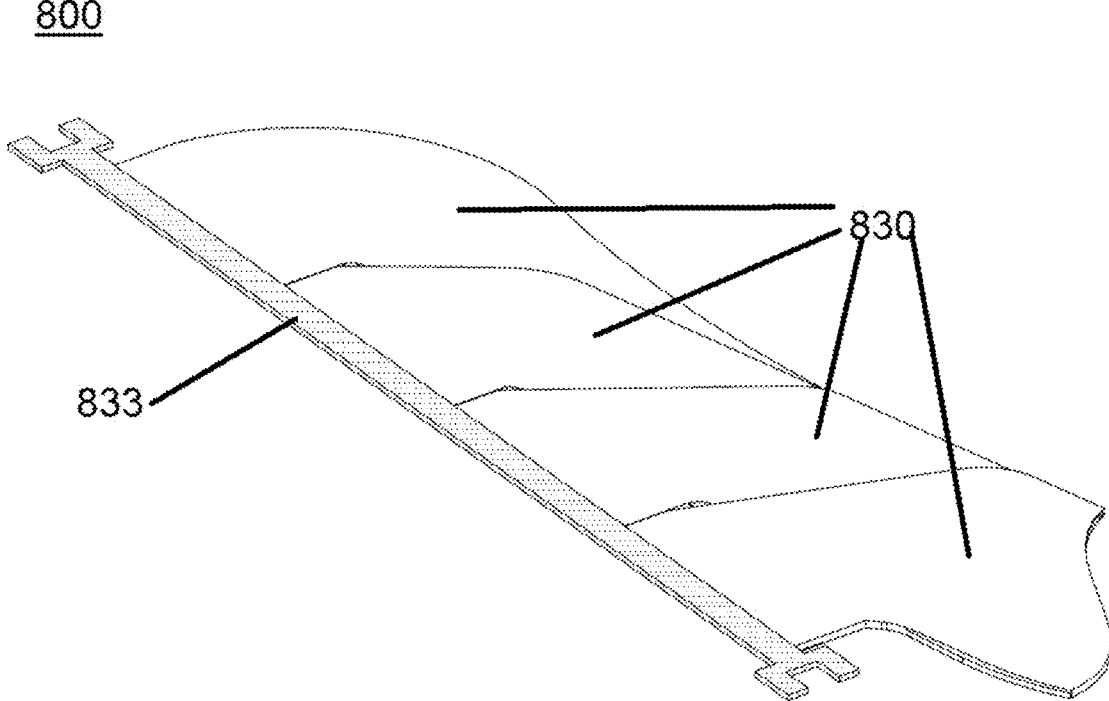
FIG. 8 depicts a flex circuit structure that can be integrated into examples of the planar linear array stacks described herein.
Figure 12:
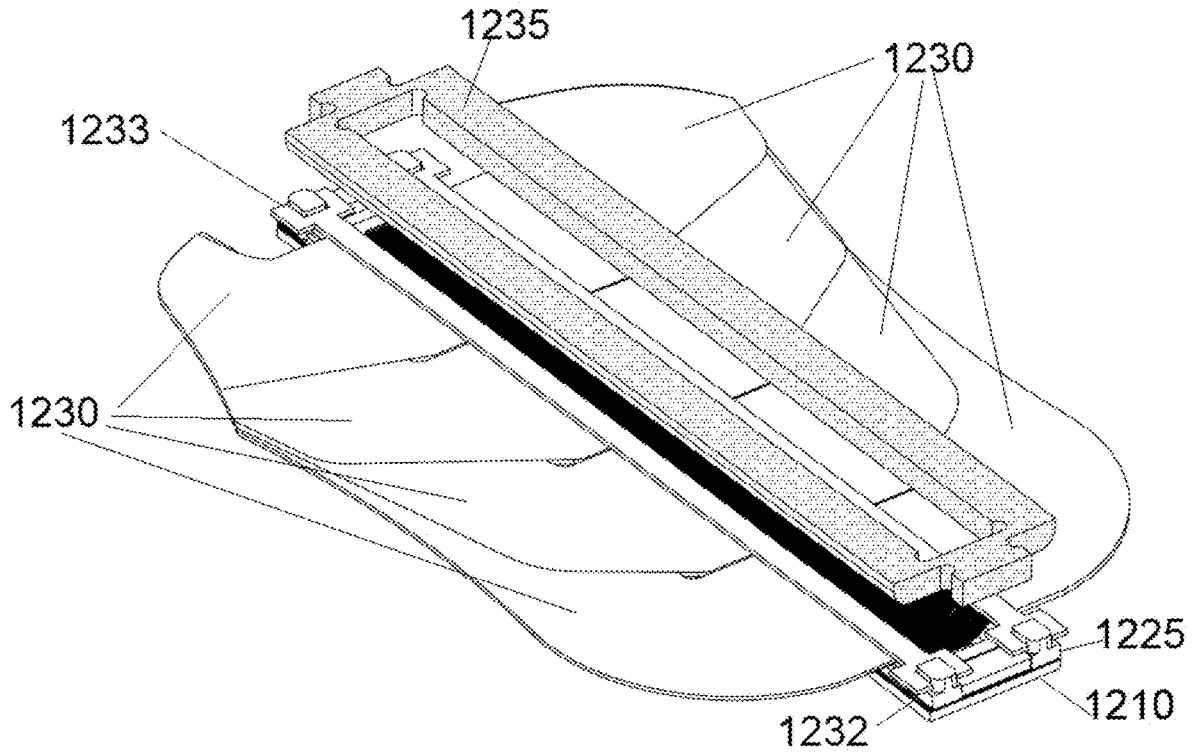
FIGS. 12 and 13 illustrate an example of an assembly of a flex bending frame with certain elements of the planar linear array described herein.
Figure 13:
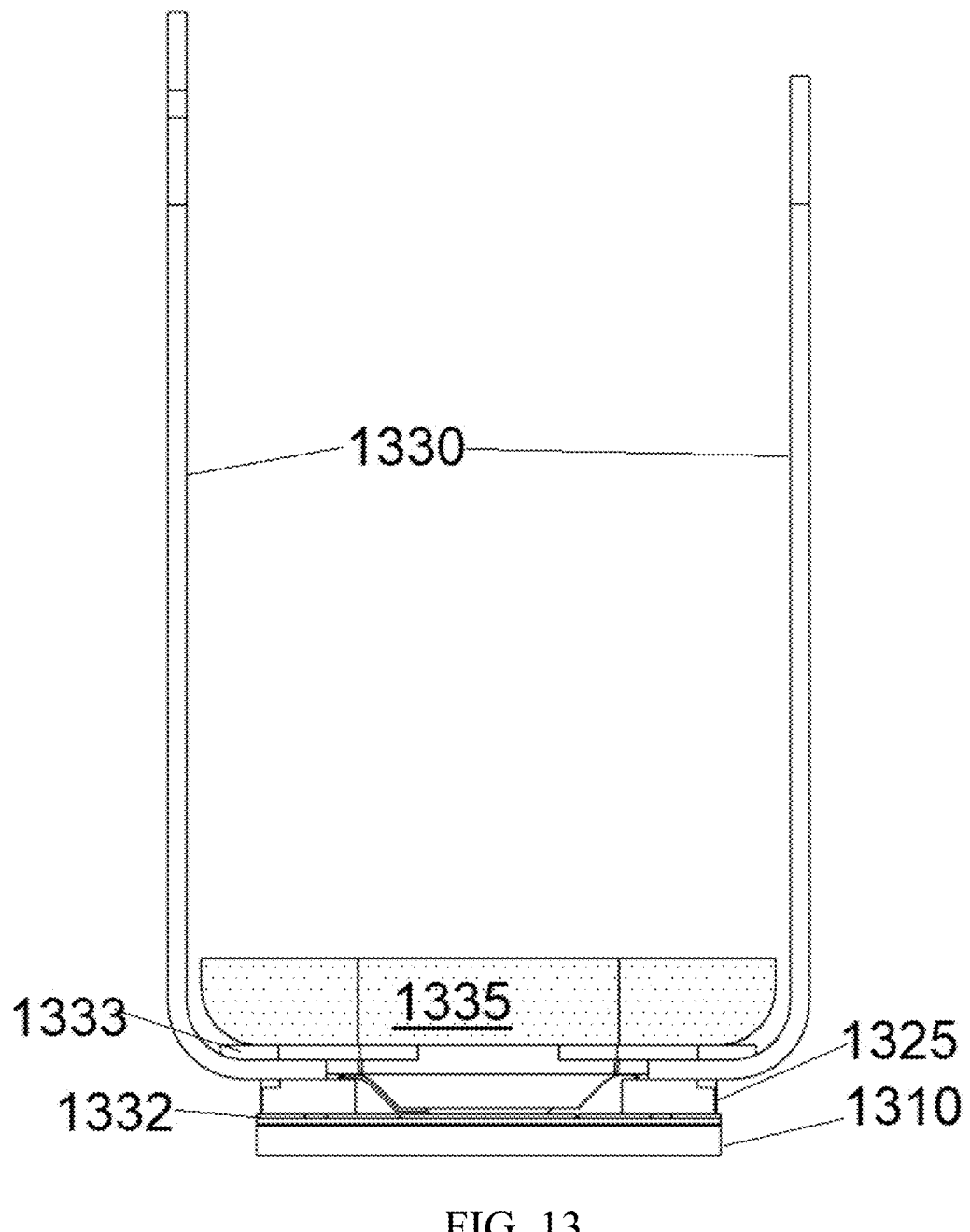
Figure 15:
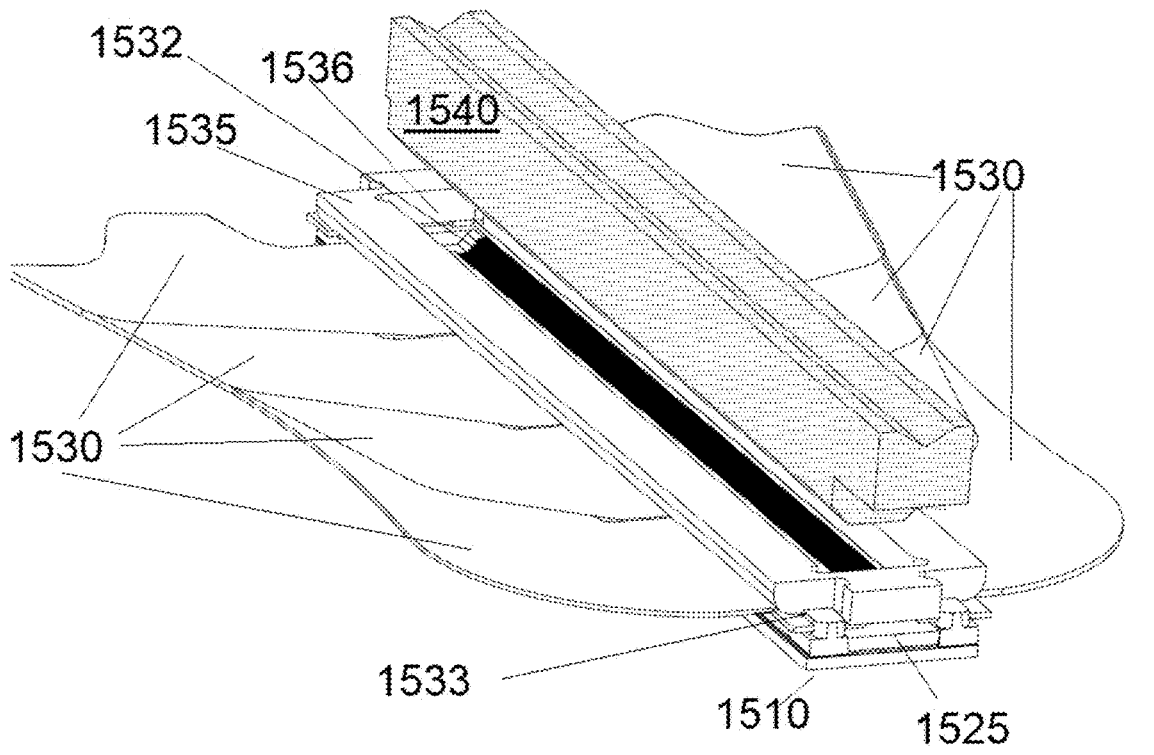
FIG. 15 illustrates a backing preform during assembly of an example of the planar linear array for a transducer disclosed herein.
Figure 20:
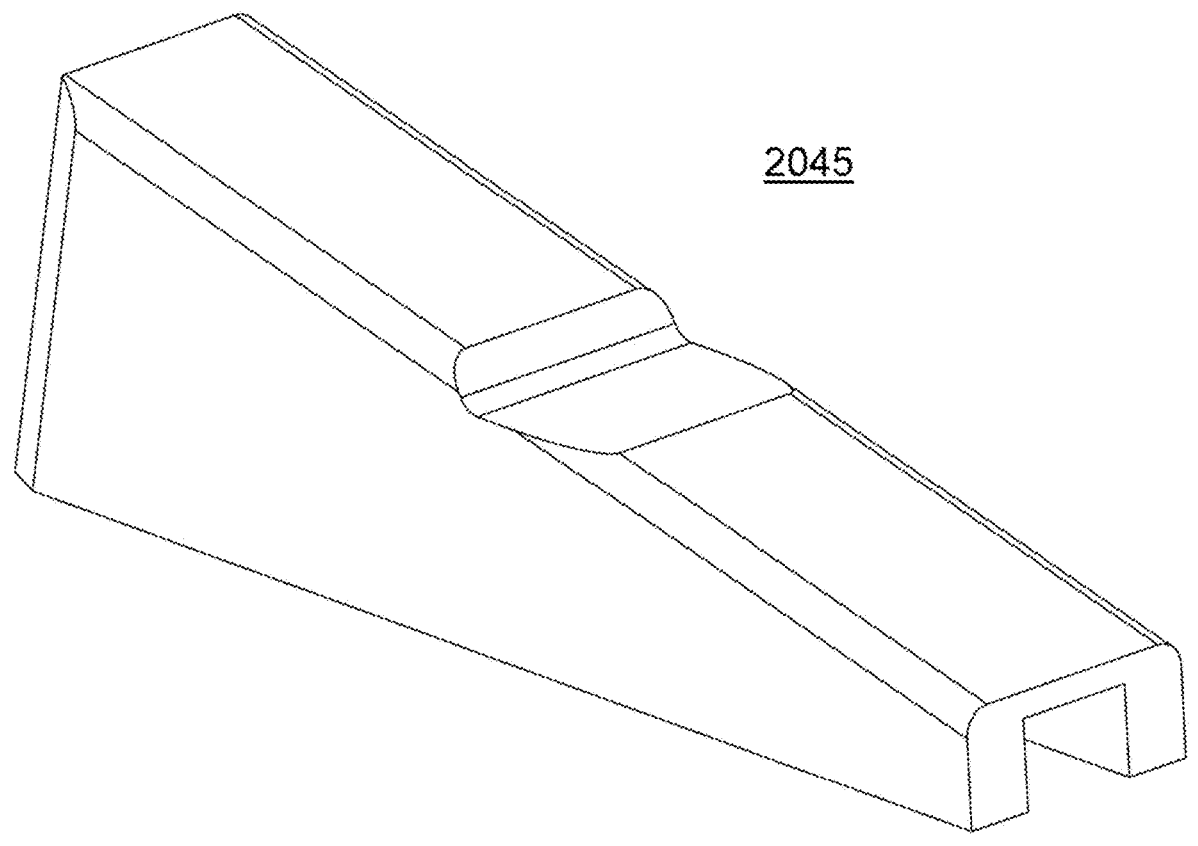
FIG. 20 depicts an example of an illustration of the bending spacer that can be integrated into certain examples of the planar linear arrays described herein.

(FIG. 1) in the planar linear arrays described herein. FIG. 6 depicts an overmould 632, which secures the flex circuits 630 to the interposer frame 625. FIG. 7 depicts an example of the interposer frame 725. FIG. 8 depicts a flex circuit structure, including a flex registration strip 833 and flex circuits 830. FIGS. 12 and 13 illustrate a flex bending frame 1235, 1335. FIG. 15 illustrates a backing preform 1540. FIG. 20 depicts a bending spacer 2045. The content of the remaining figures will also be described herein.

Referring to FIG. 1, the illustrated example of a planar linear array stack 100 includes indicators of the width in longitudinal axis 101, also referred to as longitudinal axis 101, the width axis 108, and the stack-up thickness 109. References herein to a bottom of the planar linear array stack 100 refer to the planar linear array stack 100 starting at the lens layer 110. References herein to a top of the planar linear array stack 100 refer to the planar linear array stack 100 starting at the bending spacer 145. Thus, when one describes a first element as being positioned below a second element, that means that the first element is closer to the lens layer 110 than the second element. When one describes a first element as being above a second element, that means that the first element is closer to the bending spacer 145 than the second element.

Referring to FIG. 1, planar linear array stack 100 includes a lens layer 110. This lens layer 110 can include an acoustic lens secured to a lens support structure and the lens support structure or, in some examples, the lens layer 110 can include an acoustic lens without a lens support structure. The acoustic lens utilized in various examples can be concave or convex. The acoustic lenses pictures in the figures herein are concave, by way of example, only.

The planar linear array stack 100 also includes a piezoelectric layer 120 of a piezoelectric material (e.g., PZT, PZT/SX, etc.). As will be illustrated in later figures this piezoelectric layer 120 includes a frame which is not comprised of metal (e.g., it can be made of ceramic) and referred to as a "non-metallic frame" herein which frames (e.g., surrounds) a piezoelectric material on at least two sides. In some examples, the non-metallic frame surrounds the piezoelectric material on four sides. This frame can position the piezoelectric material in a central position, relative to the longitudinal axis 101 and the width axis 108, in the planar linear array stack 100. The non-metallic frame of the piezoelectric layer 120 not only centers the piezoelectric material relative to the width axis 108 and longitudinal axis 101 in the planar linear array stack, but the frame also defines an elevational depth.

In some examples of the planar linear array stack 100, the non-metallic frame of the piezoelectric layer 120 is coupled to a portion of the lens support structure so that the acoustic lens and the non-metallic frame are oriented substantially parallel to each other along an axis of the stack-up thickness 109. In some examples, such as the planar linear array stack 100 of FIG. 1, at least one matching layer 115 separates the lens layer 110 and the piezoelectric layer 120. The matching layer 115 can provide a material buffer from acoustic impedance between elements in a transducer, including insulation elements and those elements a generated signal will be travelling through. A surface of the piezoelectric material in the piezoelectric layer 120 which is proximate to the at least one matching layer 115 can comprise at least one electrode. The surface electrically couples the piezoelectric material and the at least one matching layer 115. Above the piezoelectric layer 120 is an interposer frame 125 that positions one or more flex circuits 130. The interposer frame 125, which can be comprised of ceramic or a solid material, is not conductive but is used to anchor conductive materials and/or interconnect conductive elements within the planar linear array stack 100 and thus, enable conduction. In some examples, one adds a conductive layer to the interposer frame 125 so that the interposer frame 125 can bridge a ground connection and signal electrode connections within the planar linear array stack 100 (described below in more detail).

For ease of illustration, FIG. 1 depicts only a single flex circuit 130. As will be illustrated in later figures, multiple flex circuits can be used and these flex circuits can electrically couple the interposer frame 125 to the piezoelectric layer 120. The flex circuits 130 can be additionally coupled to a ground electrode. Although not depicted in FIG. 1, a plurality of shapes of uniform scale coated with a conductive material or comprised of a conductive material throughout (e.g., metal micro-shapes) can couple the interposer frame 125 to the flex circuits 130. Spheres are used as an example of a shape throughout, but as understood by one of skill in the art, the conductive shapes that can be utilized in various examples herein can include, but are not limited to, pyramids as well as cubes, provided that the height (e.g., stack-up thickness 109) of the shapes is uniform (when positioned). Different shapes can be mixed with each other.

In FIG. 1, the relative position of the interposer frame 125 is under (i.e., closer to the lens layer 110) the one or more flex circuits 130 and above (i.e., closer to the bending spacer 145) the piezoelectric layer 120, and a flex bending frame 135 is substantially parallel (along the stack up thickness 109 axis) to a first portion of the one or more flex circuits 130. An overmould 132 secures the flex circuits 130 to the interposer frame 125. As will be illustrated herein, a second portion of each flex circuit of the one or more flex circuits 130 is bent in the direction of the stack-up thickness 109 such that this portion of the one or more flex circuits 130 is substantially perpendicular to a surface of the flex bending frame 135 along the width axis 108 of the planar linear array 100 (e.g., this portion of the one or more flex circuits 130 is substantially perpendicular to the plane defined by the width axis 108 dimension and the longitudinal axis 101 dimension, and the surface of the flex bending frame 135 is substantially parallel to this plane) width axis 108. Thus, one can utilize the flex bending frame 135 to shape the one or more flex circuits 130 such that a portion of the bent flex circuits is perpendicular to the width axis 108 axis of the planar linear array stack 100 and bent in the direction of the stack-up thickness 109.

As illustrated in FIG. 1, both the interposer frame 125 and the flex bending frame 135 have cavities 126, 136. When stacked in the planar linear array stack 100, these cavities 126, 136 line up with each other and create an opening or cavity in a central location along the width axis 108 and the longitudinal axis 101 of the planar linear array stack 100. A portion of a backing preform 140 extends through this opening (created by the cavities 126, 136). A bending spacer 145, which aids in bending/positioning the one or more flex circuits 130, is positioned above the backing preform 140 along the stack-up thickness 109 such that a portion of each flex circuit of the one or more flex circuits 130 is substantially parallel to a surface of the bending spacer (along the width axis 108), but the other portion of the one or more flex circuits 130 is bent and hence is perpendicular to the width axis 108 of the planar linear array stack (extending in the direction of the stack up thickness 109). As aforementioned, the backing preform 140 fits the planar structure and reduces material costs; the costs are saved because the backing preform is smaller in volume than alternative structural guides and is built to accommodate the planar structure on the planar linear array. The backing preform 140 locates the bending spacer which is used to guide the one or more flex circuits 130.

FIGS. 2 and 3 both depict examples of a lens layer 210, 310 (e.g., FIG. 1, 110), which can be integrated into examples of the planar linear array stacks described herein, including but not limited to, the planar linear array stack 100 of FIG. 1. A difference between the lens layer 210 of FIG. 2 and the lens layer 310 of FIG. 3 is a lens support structure 212, 312 utilized to position an acoustic lens 211, 311 in each example.

In the lens layer 210 of FIG. 2, the support structure 212 for the acoustic lens 211 includes a first bar 213*a* and a second bar 213*b*, which are situated on opposing sides of the acoustic lens 211. The acoustic lens 211 can be comprised of a dielectric material, including but not limited to, Rexolite®. The material of the support structure 212 can be selected based on having a similar coefficient of thermal expansion as the acoustic lens 211, to minimize any warping, including bowing, in the lens layer 210 when it is subjected to heat (e.g., during use of the ultrasound transducer). Avoiding differential expansion between the acoustic lens 211 and the support structure 212 is desirable for the integrity and longevity of the planar linear array stack 100 (FIG. 1) and any transducer into which the planar linear array stack 100 (FIG. 1) is integrated. Materials comprising the support structure 212 can include, but are not limited to, ceramic, plaster with ceramic, and plaster with metal (e.g., silver, gold).

As understood by one of skill in the art, an acoustic lens 211 can be used to focus an ultrasound beam to improve the sensitivity of the image. To this end, one creates a certain curvature (e.g., ROC) in the acoustic lens 211 to focus the ultrasound beam properly. Thus, the acoustic lens 211 of FIG. 2 includes a curvature 214. The support structure 212 in the lens layer 210, when integrated into a planar linear array stack (e.g., FIG. 1, 100), positions the curvature 214 at similar width axis 108 and longitudinal axis 101 coordinates as the piezoelectric material in the piezoelectric layer (e.g., FIG. 1, 120). This positioning centers the acoustic lens 211 and the piezoelectric material along the width axis 108 and longitudinal axis 101 of the planar linear array stack 100.

In the lens layer 310 of FIG. 3, the support structure 312 for the acoustic lens 311 includes a frame 313, situated around the perimeter of the acoustic lens 311. The acoustic lens can be comprised of a dielectric material, including but not limited to, Rexolite®. As with the support structure 212 of FIG. 2, in the lens layer 310 of FIG. 3, the material of this support structure 312 can likewise be selected based on having a similar coefficient of thermal expansion as the acoustic lens 311, to minimize any warping, including bowing, in the lens layer 310 when it is subjected to heat (during use of the ultrasound transducer). Avoiding differential expansion between the acoustic lens 311 and the support structure 312 is desirable for the integrity and longevity of the planar linear array stack 100 (FIG. 1) and any transducer into which the planar linear array stack 100 (FIG. 1) is integrated. Materials comprising the support structure 312 can include, but are not limited to, ceramic, plaster with ceramic, and plaster with metal (e.g., silver, gold). The acoustic lens 311 can include a curvature 314 and the portions of the support structure 312 that abut the curvature 314 can also include this shaping, as is depicted in FIG. 3. The support structure 312 in the lens layer 310, when integrated into a planar linear array stack (e.g., FIG. 1, 100), positions the curvature 314 of the lens at a central location along the width axis 108 (FIG. 1) and longitudinal axis 101 (FIG. 1) of the planar linear array stack.

FIG. 4 depicts an example of a piezoelectric layer 420, another example of which is depicted as a piezoelectric layer 120 in FIG. 1. The top view provided in FIG. 4 depicts an example of a piezoelectric layer 420 that includes a non-metallic frame 421, which can be comprised of an insulating material, including but not limited to, ceramic. In the context of this example, the non-metallic frame 421 serves at least one of three functions: 1) it centers the piezoelectric material 422 along the longitudinal axis 101 (FIG. 1) and the width axis 108 (FIG. 1) of the planar linear array 100 (FIG. 1); 2) it defines the elevation (e.g., FIG. 1, 101) of the planar linear array 100 (FIG. 1); and 3) it includes ground trenches 423 to bring ground connections from the front to the back of the piezoelectric layer 420 (forming part of a return signal path).

The non-metallic frame 421 encloses a piezoelectric material 422 (e.g., PZT, PZT/SX, etc.). The piezoelectric layer 420 serves as a pure 1-3 composite used in a high frequency transducer. To set the shape, size, and thickness of the piezoelectric material 422, one can pre-dice the material itself into sections or array elements of the desired shape, size, and thickness for the desired use. In one non-limiting example, the piezoelectric material 422 is cut to a precise size of 46.0 mm×2.8 mm, with the elevation width of 2.4 mm. The PZT is then bonded to the non-metallic frame 421 with a bonding agent (e.g., glue). With this structure, a pure 1-3 composite can be made and used in the high frequency transducer. The non-metallic frame 421 holds the piezoelectric material 422 in place such that the piezoelectric material 422 is centered on the width axis 108 (FIG. 1) and longitudinal axis 101 (FIG. 1). The non-metallic frame 421 defines the even elevation width by controlling the width of the central opening, based on positioning according to the width axis 108 (FIG. 1) and longitudinal axis 101 (FIG. 1) (into which the piezoelectric material 422 is placed). For example, the non-metallic frame 421 can maintain the consistency of the elevation width. The non-metallic frame 421 also provides a ground path from the piezoelectric material 422 to the flex circuits (e.g., FIG. 1, 130) via ground trenches 423. The electrical connectivity within the planar linear array is discussed further in the discussion of FIGS. 9A and 9B, collectively referred to herein as FIG. 9.

The non-metallic frame 421 maintains the rigidity of the piezoelectric material 422, improving the life of the piezoelectric material 422, which serves as the active area of the piezoelectric layer 420. As noted above, one can size the piezoelectric material 422 in accordance with the intended use of the resultant transducer. In the example illustrated in FIG. 4, the non-metallic frame 421 surrounds the piezoelectric material 422 on four sides, but in some examples, the non-metallic frame 421 surrounds the piezoelectric material 422 on two sides. In some examples, the non-metallic frame 421 positions the piezoelectric material 422, centering it relative to the width axis 108 (FIG. 1) and the longitudinal axis 101 (FIG. 1) in a planar linear array stack (e.g., FIG. 1, 100). As with the lens layer (e.g., FIGS. 2 and 3, 210 and 310, respectively), the element centered relative to the width axis 108 (FIG. 1) and the longitudinal axis 101 (FIG. 1) by a support structure can be affixed to the support structure using a bonding agent, such as a glue or epoxy that will not denature during use of the resultant transducer.

One can size the piezoelectric material 422 in accordance with the intended use of the resultant transducer. The piezoelectric material 422 can vary in size and in some examples, the piezoelectric material 422 is sized similarly to the acoustic lens (e.g., FIGS. 2 and 3, 211 and 311, respectively). The non-metallic frame 421 can position the piezoelectric material 422 so that it is at substantially the same location as the acoustic lens (e.g., FIGS. 2 and 3, 211 and 311, respectively) relative to the width axis 108 (FIG. 1) and the longitudinal axis 101 (FIG. 1) of the planar linear array stack, but at different coordinates on an axis representing the stack up thickness 109 (FIG. 1). Thus, in these examples, the lens layer (e.g., FIGS. 2 and 3, 210 and 310, respectively) and piezoelectric layer 420 are substantially parallel to each other in the planar linear array stack (e.g., FIG. 1, 100).

The non-metallic frame 421 can include, as illustrated in FIG. 4, one or more ground trenches 423. To fabricate the ground trenches 423 in the non-metallic (e.g., ceramic) frame 421, as will be discussed later with respect to a method of manufacturing planar linear array stacks disclosed herein, in an example one drills (e.g., machines or mills) trenches in the non-metallic frame 421, fills the trenches with a first conductive material metal (e.g., silver, gold), and coats the filled trenches with a second conductive material, creating ground trenches 423. These conductive materials can be the same or they may vary. For example, one can coat the ground trenches with gold and fill them with a solver epoxy. Providing ground trenches 423 in the non-metallic frame 421 represents a simplified ground connection for the array, when compared to ground connections in existing arrays. Signal ground can be challenging to fabricate when working with piezoelectric materials because an exposed electrode is generally utilized, which can interfere with the desired planar quality of the array. In the examples herein, the non-metallic frame 421 works as an insulator around the ground trenches 423, which can be positioned flush to the upper surface of the piezoelectric layer 420, maintaining the planar (flat) quality of the array.

Figure 23:
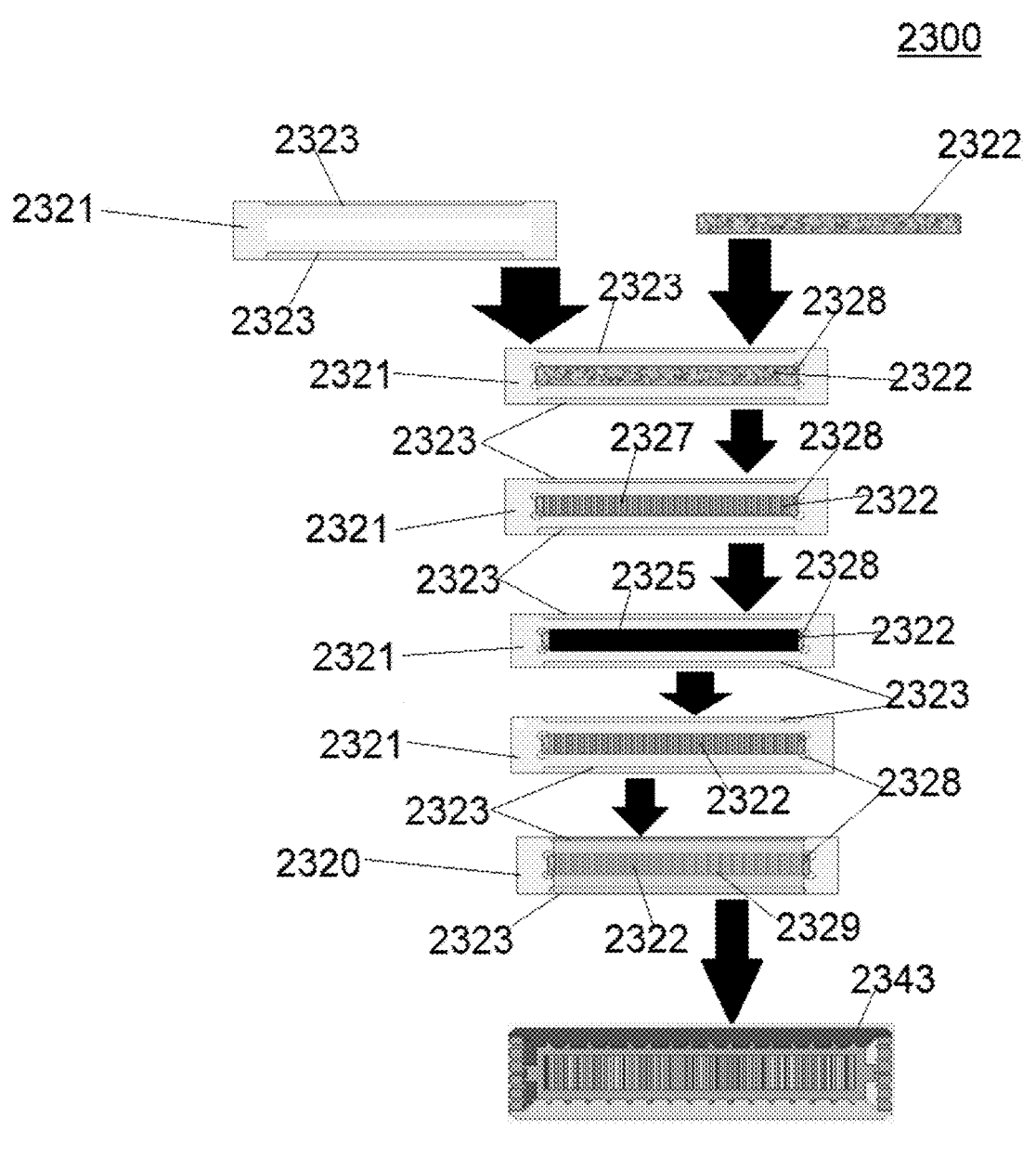
FIG. 23 illustrates an example of a technique for forming a piezoelectric layer for use in a transducer that can comprise an example of the planar linear array stack described herein.

Returning to the piezoelectric material 422 itself, the piezoelectric material 422 comprises one or more kerfs cut into a pattern. The timing of cutting the patterns into the piezoelectric material 422 can vary. In some examples, one patterns the piezoelectric material 422 before assembling the piezoelectric layer 420. In other examples, one patterns the piezoelectric material 422 after assembling the piezoelectric layer 420. One can select different patterns depending on the intended use of the transducer. In still other examples, one patterns the piezoelectric material 422 both before and after assembling the piezoelectric layer 420. FIG. 23, which will be discussed later herein, illustrates aspects of a method of forming an example of a piezoelectric layer 420, 2320. The piezoelectric layer 2320 can be integrated into different stacks for use in different ultrasound technologies such as the planar linear array 100 (FIG. 1) in a non-limiting example.

FIG. 5 illustrates different patterns that a laser can be used to form in the piezoelectric material 422, e.g., either before or after one integrates the piezoelectric material 422 into the piezoelectric layer 420 by bonding the piezoelectric material 422 to the non-metallic frame 421, including by gluing the non-metallic frame 421 to the piezoelectric material 422 or vice versa. The patterns include a first pattern 502, a second pattern 503, and a third pattern 504. The elevation 505 (e.g., longitudinal axis 101, FIG. 1) and thickness 506 (e.g., stack up thickness 109, FIG. 1) of the piezoelectric material in each pattern are also illustrated in FIG. 5. As understood by one of skill in the art, one can pattern a piezoelectric material with conventional sub-dice pattern where a transducer element is divided lengthwise down its center by a single sub-dice kerf cut. This sub-dice kerf cut has the same length as the transducer element. As will be appreciated by those skilled in the art, the width/height ratio of a transducer element should be less than or equal to the "golden ratio" of about 0.6 to minimize lateral vibrational modes in the PZT. As illustrated in FIG. 5, each pattern includes a main kerf 507, the aforementioned sub-dice kerf, subdividing the dielectric (e.g., piezoelectric) material. One can cut the main kerf 507 between each element at the pitch. The sub-diced kerf is cut in the middle of each element. In addition to the main kerf 507, the second pattern 503 also includes a square pattern while the third pattern 504 also includes a parallelogram pattern. These patterns can be utilized in a 90-micron pitch array, for example. A laser, including but not limited to an excimer laser, which, in some examples, can machine the piezoelectric material 422 to create these kerfs. For example, the laser can cut an 8-10-micron kerf to a depth of −100 microns in piezoelectric materials such as PZT ceramics, forming kerfs in the piezoelectric material 422 of about 3-5 microns. This measurement is provided merely as an example and not to suggest any limitations. In some examples, the laser is also used to perform a back-cut to maintain the uniformity of the kerf width along the vertical structures.

As illustrated in FIG. 1, the planar linear array stack 100 can include an interposer frame 125 that positions one or more flex circuits 130. FIG. 6 depicts a structure 600 that serves to secure flex circuits in the planar linear array stack. This structure 600, depicted in FIG. 6 as an exploded view, includes the aforementioned interposer frame 625 (e.g., FIG. 1,125), the aforementioned flex circuits 630 (e.g., FIG. 1, 130) and an overmould 632, which secures the flex circuits 630 to the interposer frame 625. In some examples, the overmould 632 includes electrodes on its surface, and the electrodes can include a conductive material, such as a metal (e.g., gold, silver). The electrodes can become a channel, including but not limited to a gold channel. For example, the overmould can comprise a gold foil. The flex circuits 630 include traces (not pictured in FIG. 6) of a conductive material (e.g., copper (Cu), gold, and/or silver, etc.) on certain surfaces. Flex registration strips are not included in FIG. 6 and are discussed below, but in this example of FIG. 6, the interposer frame 625 is positioned under the one or more flex circuits 630, while the overmould 632 helps to secure the one or more flex circuits 630 to the interposer frame 625.

FIGS. 7 and 8 provide additional insight into aspects of FIG. 6. For ease of understanding, FIG. 7 depicts just the interposer frame 725 itself, as the interposer frame 625 is slightly obscured in FIG. 6. Meanwhile, FIG. 8 depicts a flex circuit structure 800 that includes a flex registration strip 833 and flex circuits 830. In various examples of the planar linear array described herein, a flex registration strip 833 is positioned between the interposer frame 625 and a flex bending frame 135 (e.g., FIG. 1), substantially parallel to part of the one or more flex circuits 830. As illustrated in FIG. 8, in some embodiments of the planar linear array described herein, each flex registration strip 833 joins four flex circuits 830. The flex registration strip 833 provides precision alignment to the array elements at a 90-micron pitch (e.g., a linear alignment).

Figure 9A:
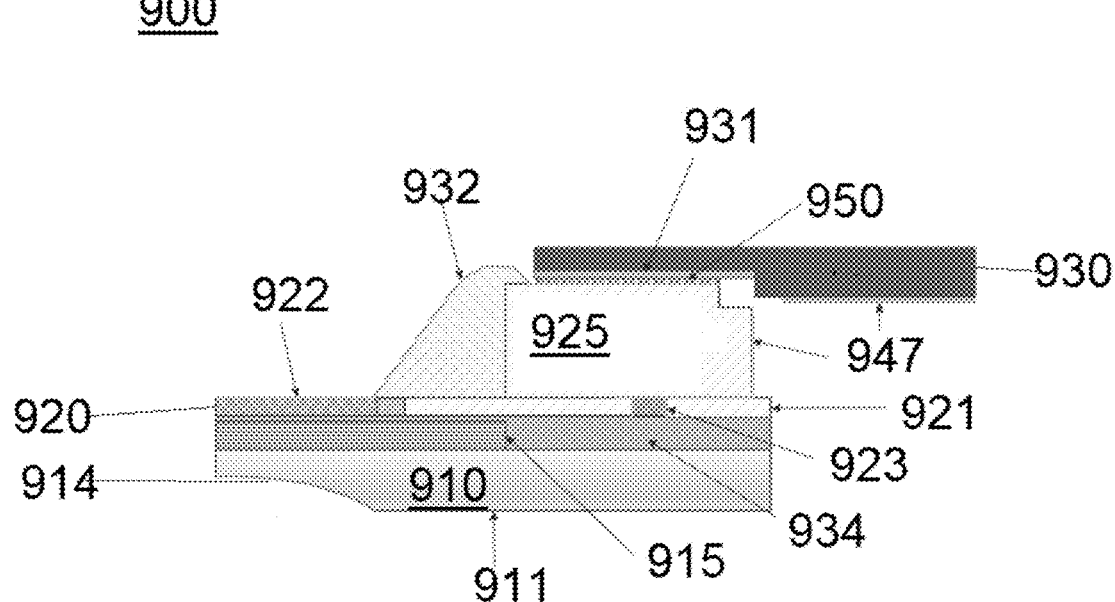
FIGS. 9A, 9B, and 10 provide views of various elements of the planar linear array stacks described herein.
Figure 9B:
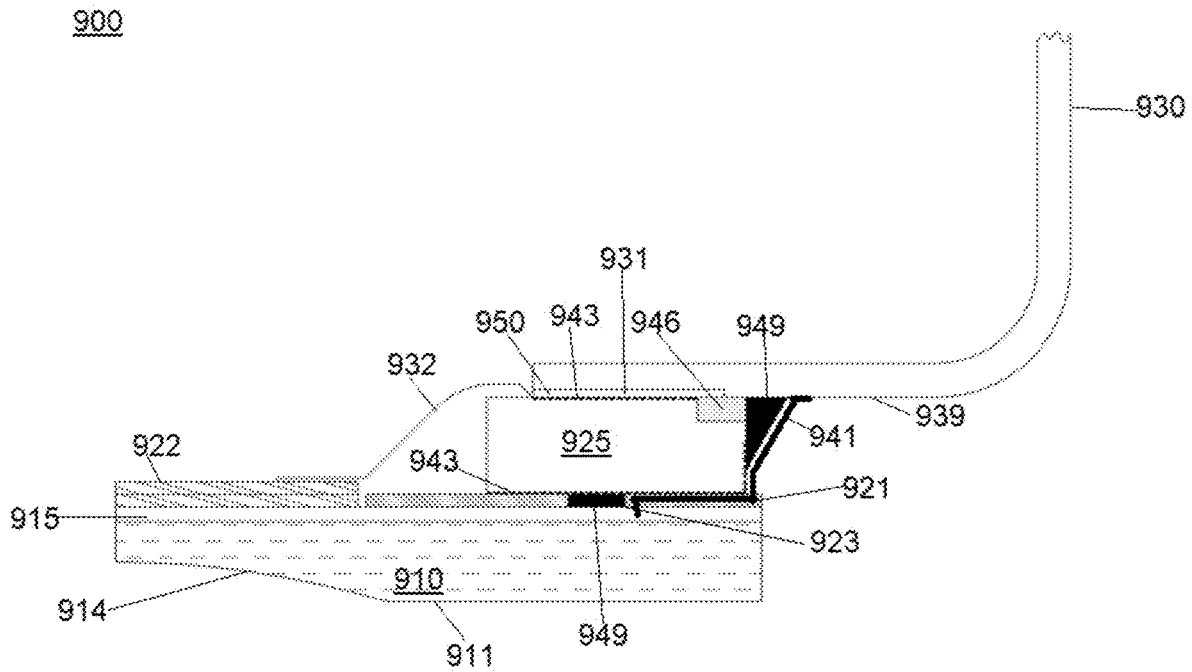
Figure 10:
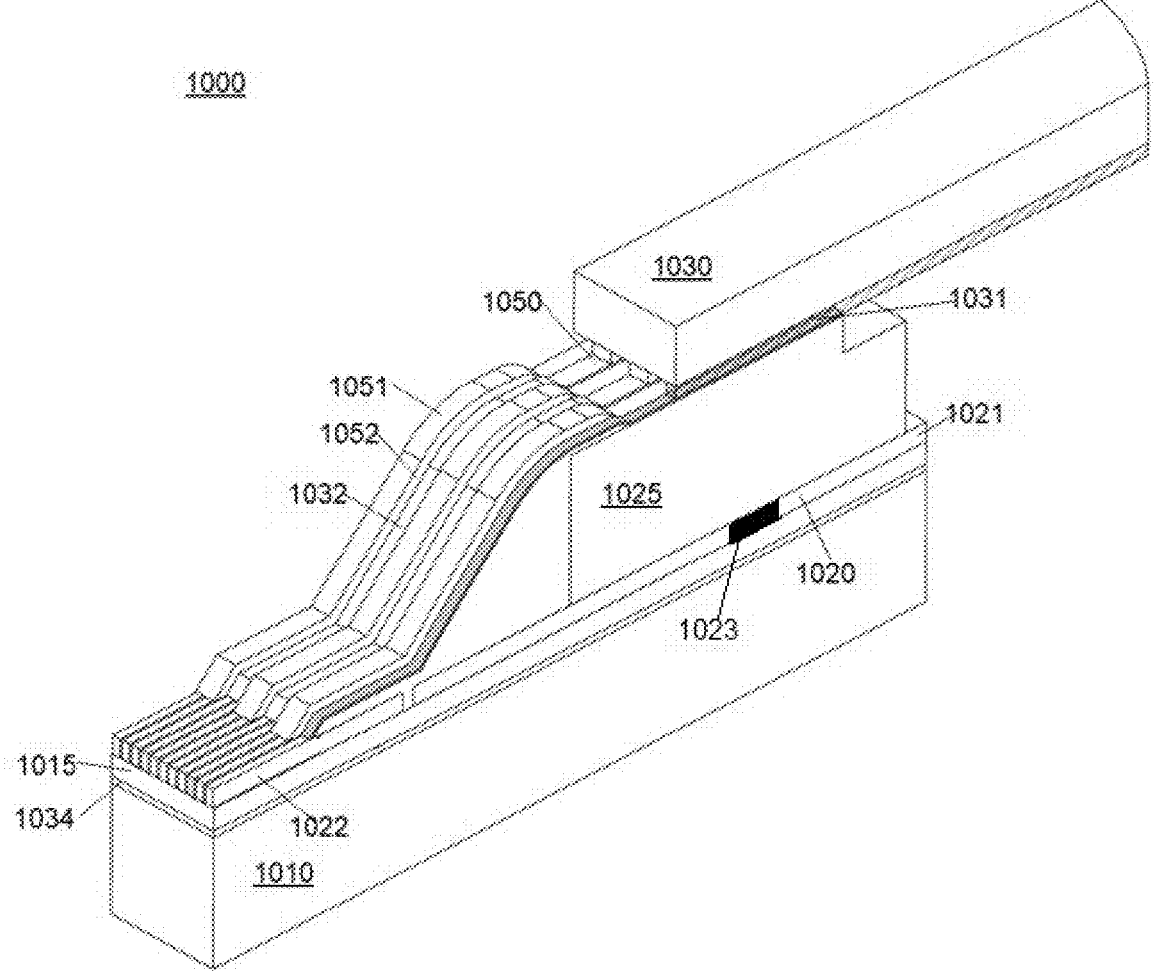

FIGS. 9 and 10 provide alternative views (when compared to FIG. 1) of various elements of the planar linear array stack described herein. These views are provided in advance of describing a structure utilized in some embodiments to transmit an electrical signal from a surface of the interposer frame 625 (FIG. 6) to traces on a surface of the one or more flex circuits 630 (FIG. 6), conductive shapes of uniform scale 950, 1050 (FIG. 9, FIG. 10). FIG. 9B provides an additional illustration of an electrical connection of the ground from the piezoelectric material to the one or more flex circuits 930. Additionally, while FIG. 9A illustrates the one or more flex circuits 930 before they are bent, FIG. 9B illustrates the one or more flex circuits 930 after they are bent. The conductive shapes of uniform scale (950, 1050 (FIG. 9, FIG. 10)) are illustrated herein as spheres, but the spheres are provided as a non-limiting example as the shapes can include pyramids, cubes, etc. The shapes comprising the conductive shapes of uniform scale in a planar linear array stack can be uniform or mixed, and they can be of uniform height along the stack up thickness 109 axis (FIG. 1).

Starting from the bottom of the portion of the planar linear array 900, 1000, as depicted in FIGS. 9 and 10 and moving upwards (e.g., FIG. 1, from the lens layer 110 to the bending spacer 145, along the stack up thickness 109 axis), this array includes a lens layer 910, 1010 that includes an acoustic lens 911 with a curvature 914. Above the top surface of the lens layer 910, 1010 is one or more matching layers 915, 1015. Lens bonding glue 934, 1034 bonds an upper surface of the lens layer 910 to the piezoelectric layer 920 or a matching layer 1015 to the piezoelectric layer 1020. The piezoelectric layer 920, 1020 includes piezoelectric material 922, 1022 with electrodes on both sides, a non-metallic frame 921, 1021, and ground trenches 923, 1023. The flex circuits 930, 1030 connect 947 to a ground electrode after they are bent. This connection is described and illustrated in greater detail in FIG. 9B.

An interposer frame 925, 1025, which includes conductive electrodes and/or traces (e.g., gold, copper, silver) is located on a horizontal plane above (relative to the stack up thickness 109, FIG. 1) the piezoelectric layer 920, 1020. In FIGS. 9A and 10, the flex circuits 930, 1030 are illustrated before being bent, which is why the whole of each flex circuit 930, 1030 is parallel to the piezoelectric layer 920 (meaning different coordinates along the stack up thickness 109 axis but shared coordinates relative to the width axis 108 and longitudinal axis 101, FIG. 1). In FIG. 9B, the flex circuits 930 are illustrated after having been bent. The interposer frame 925, 1025, in this example, includes conductive electrodes and/or traces (e.g., gold, copper, silver). An overmould 932, 1032 is on a surface that includes an upper surface of the interposer frame 925. The overmould comprises electrodes (e.g., gold) on its upper surface. As illustrated in FIG. 10, the overmould 1032 structure includes separation ridges 1051 and trenches 1052 that are lower than the separation ridges 1051. These trenches 1052 are coated with a conductive material, including but not limited to, gold. The interposer frame 1025 includes copper fingers 1031.

The interposer frame 925, 1025 is electrically coupled to the one or more flex circuits 930, 1030 via one or more conductive shapes of uniform scale 950, 1050 coated with a conductive material (e.g., gold, silver, etc.). In this non-limiting example, the surface of the interposer frame 925, 1025 is in contact with the conductive shapes of uniform scale 950, 1050, and includes one or more conductive traces. The conductive shapes of uniform scale 950, 1050 conduct an electrical signal from a surface of the interposer frame 925, 1025 in contact with the conductive shapes of uniform scale 950, 1050, to traces on a surface of the one or more flex circuits 930, 1030 in contact with the conductive shapes of uniform scale 950, 1050. Each shape can be comprised of a dielectric material and coated uniformly with the conductive material. When the array is oriented as it is in the example in FIG. 9, the conductive shapes of uniform scale 950 form a vertical electrical connection.

FIG. 9B illustrates various elements of the planar linear array 900 but focuses on the electrical connection (depicted in FIG. 9A as connection 947) of the ground from the piezoelectric layer 920 to the one or more flexes 930. FIG. 9B illustrates an examples of a portion the planar linear array 900 with the one or more flexes 930 bent into their final configuration (FIG. 9B illustrates a single flex to represent one or more flexes for simplicity of illustration). FIG. 9B also includes illustrations of insulating and conductive portions of the planar linear array 900. In FIG. 9B, an electrical path 941 illustrates the connection 947 (e.g., FIG. 9A).

The electrical path 941 is a ground path that forms a return signal path. The electrical path 941 illustrates the ground and its path via a ground plane 939 of the one or more flexes 930, via a conductive layer 943 on the interposer frame 925 (as discussed earlier, as a conductive layer, the interposer frame 925 includes conductive electrodes and/or traces (e.g., gold, copper, silver)), and in the ground trenches 923 on the piezoelectric layer 920. The ground path, the electrical path 941, progresses from the ground trenches 923 on the piezo-electric layer 920, to the non-metallic frame 921, via the conductive electrodes on the interposer frame 925, to the one or more flexes 930. The ground trenches 923 comprise a conductive material, including but not limited to an epoxy. In this example, the interposer frame 925 includes an electrically insulating material 946, including but not limited to an epoxy as well as an electrically conductive material 949, which can also be an epoxy. The conductive material 949 can be adjacent to the electrical path 941 while the electrically insulating material 946 bridges a portion of the conductive layer 943 on the interposer frame 925 and the conductive material 949. A connection between the conductive layer 943 on the interposer frame (which can include copper fingers 931), and the one or more flexes 930 can be bridged by conductive shapes of uniform scale 950.

Figure 11:
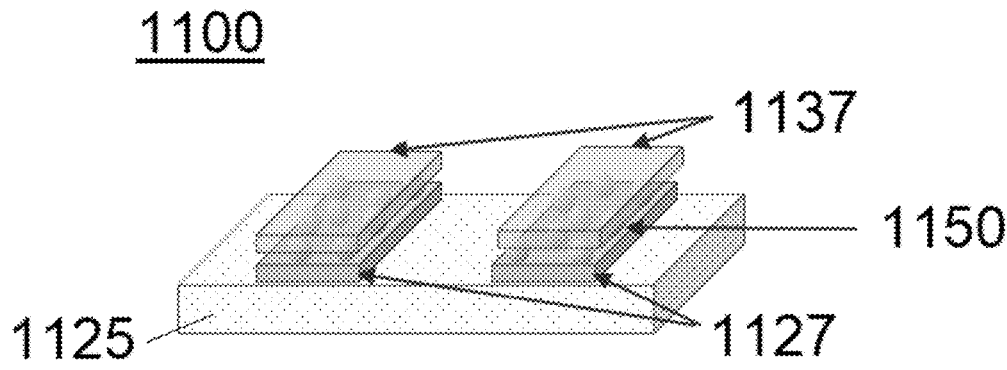
FIG. 11 illustrates an example of a connection of the interposer frame to traces on a surface of the one or more flex circuits in some examples the planar linear array described herein.

FIG. 11 provides a more detailed example of the connection 1100 of the interposer frame 925, 1025 to traces on a surface of the one or more flex circuits 930, 1030 (these traces are illustrated in FIG. 9B as a ground plane 939). One dopes the conductive shapes of uniform scale 1150 with bonding glue and situates the conductive shapes of uniform scale 1150 between the interposer frame and the flex circuits. Specifically, the conductive shapes of uniform scale 1150 electrically connect traces (e.g., Cu fingers) 1137 on each flex circuit (not shown in FIG. 11) and traces (e.g., gold traces) on the interposer frame 1125. Each shape 1150 in this example is comprised of a dielectric material (e.g., glass, polymer) and coated uniformly with a conductive material (e.g., copper, gold, silver, titanium, etc.).

Figure 14:
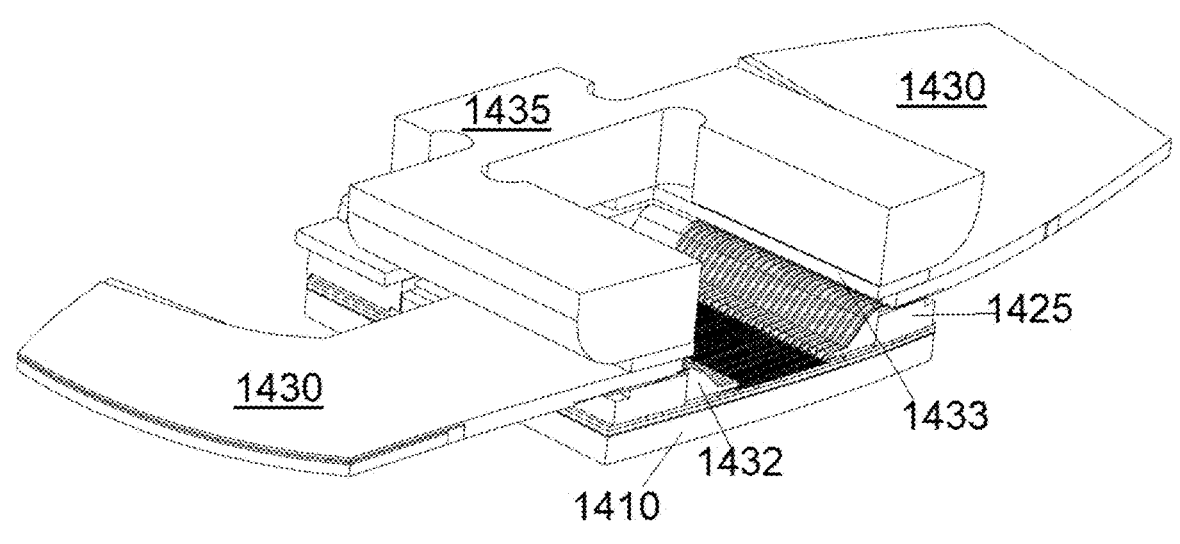
FIG. 14 illustrates a blown-up view of a flex bending frame integrated into examples of the planar linear array stacks described herein.

FIGS. 12-14 illustrate an example of the flex bending frame 135 (FIG. 1). FIG. 12 shows the assembly of the flex bending frame 1235 with certain elements of the planar linear array described herein while FIG. 13 shows these portions of the planar linear array after the flex bending frame 1335 is used to bend the flex circuits 1330. FIG. 14 illustrates a blown-up view of the flex bending frame 1435. One can attach the flex bending frame 1235, 1335, 1435 to the top of the flex circuits 1230, 1330, 1430. The flex bending frame 1235, 1335, 1435 provides a consistent and reliable guide for bending the flex circuits 1230, 1330, 1430 and secures their bonding. To illustrate the orientation of the flex bending frame 1235, 1335, 1435 within the array (e.g., FIG. 1, 100), FIGS. 12-14 illustrate elements described in other figures, such as the lens layer 1210, 1310, 1410, the overmould 1232, 1332, 1432, the interposer frame 1225, 1325, 1425, and the flex registration strips 1233, 1333, 1433.

In general, the flex bending frame 1235, 1335, 1435 guides the flex circuits 1230, 1330, 1430 as they are bent.

Figure 16:
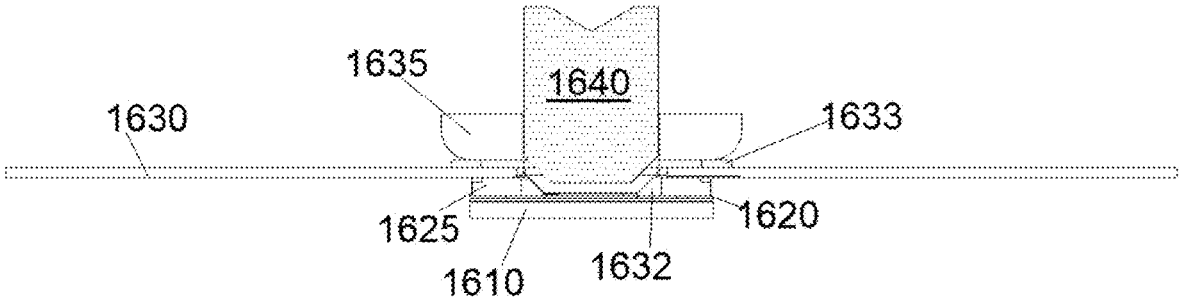
FIG. 16 illustrates a view of an example of the planar linear array for a transducer disclosed herein, post-assembly.

The backing preform 140 and its orientation with the planar linear array for a transducer disclosed herein are further illustrated in FIGS. 15 and 16 (1540, 1640). While FIG. 15 illustrates the backing preform 1540 during assembly of an example of the planar linear array for a transducer disclosed herein, FIG. 16 illustrates a view of an example of the planar linear array for a transducer disclosed herein, post-assembly, to illustrate the relative orientation of the backing preform 1640. Also illustrated in both FIGS. 15 and 16, as parts of the example of the planar linear array illustrated in both figures, is a lens layer 1510, 1610 and an interposer frame 1525, 1625 (to which one or more flex circuits 1530, 1630 are attached) utilizing flex registration strips 1533, as well as the overmould 1532 (in cavity 1536), 1632, as described earlier herein. The number of flex circuits 1530, 1630 in FIGS. 15 and 16, as with all figures, is just provided by way of example. The number of flex circuits 1530, 1630, as well as the number of flex circuits 1530, 1630 affixed to each flex registration strip 1533, 1633, can vary. In FIG. 16, the flex circuits 1630 have not yet been bent, using the flex bending frame 1535, 1635. Because of the vantage point of FIG. 16, the piezoelectric layer 1620 oriented above the lens layer 1610 is included to illustrate the elements of this example of the planar linear array discussed herein and their relative positioning to each other.

Figure 17:
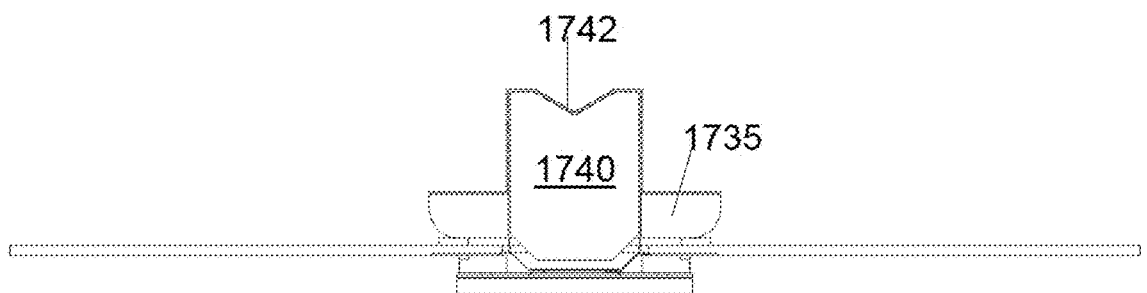
FIG. 17 illustrates an example of a shielding element that is included in certain examples of the planar linear arrays described herein.

In some embodiments of the present invention, to reduce electromagnetic interference (EMI), a machine or individual deposits a layer of a conductive material on the backing preform 1540, 1640. For example, one can wrap the backing preform 1540, 1640 with a conductive tape, including but not limited to, a copper tape, to create an EMI shielding element and to bridge the return signal to ground. Alternatively, in some embodiments, a layer of a conductive materials can be deposited over surfaces of the backing preform and over the flex bending frame. FIG. 17 illustrates an example of a shielding element 1742 added to an example of a planar linear array described herein. In this example, the shielding element 1742 is a conductive coating (e.g., copper) deposited on an upper surface of the backing preform 1740 and on an upper surface of the flex bending frame 1735.

Another element of planar linear arrays described herein that is included in some embodiments is a bending spacer 145 (FIG. 1). The bending spacer 145 aids an individual or machine assembling a planar linear array for a transducer in bending and/or positioning the one or more flex circuits 130 (FIG. 1). An individual or machine places the bending spacer 145 (FIG. 1) above the backing preform 140 (FIG. 1) so that the one or more flex circuits 130 (FIG. 1), when bent, are substantially parallel to a stack up thickness 109 axis. Returning to FIG. 9B, when the one or more flex circuits 930 are bent, a first portion of each of the one or more flex circuits 930 remains parallel to the piezoelectric layer along the longitudinal axis 101 (FIG. 1) while a second portion of the one or more flex circuits 930 is bent to be perpendicular to the piezoelectric layer along the longitudinal axis 101 (FIG. 1). The portion that is parallel to the piezoelectric layer along the longitudinal axis 101 (FIG. 1) comprises the copper fingers 931, 1031.

Figure 18:
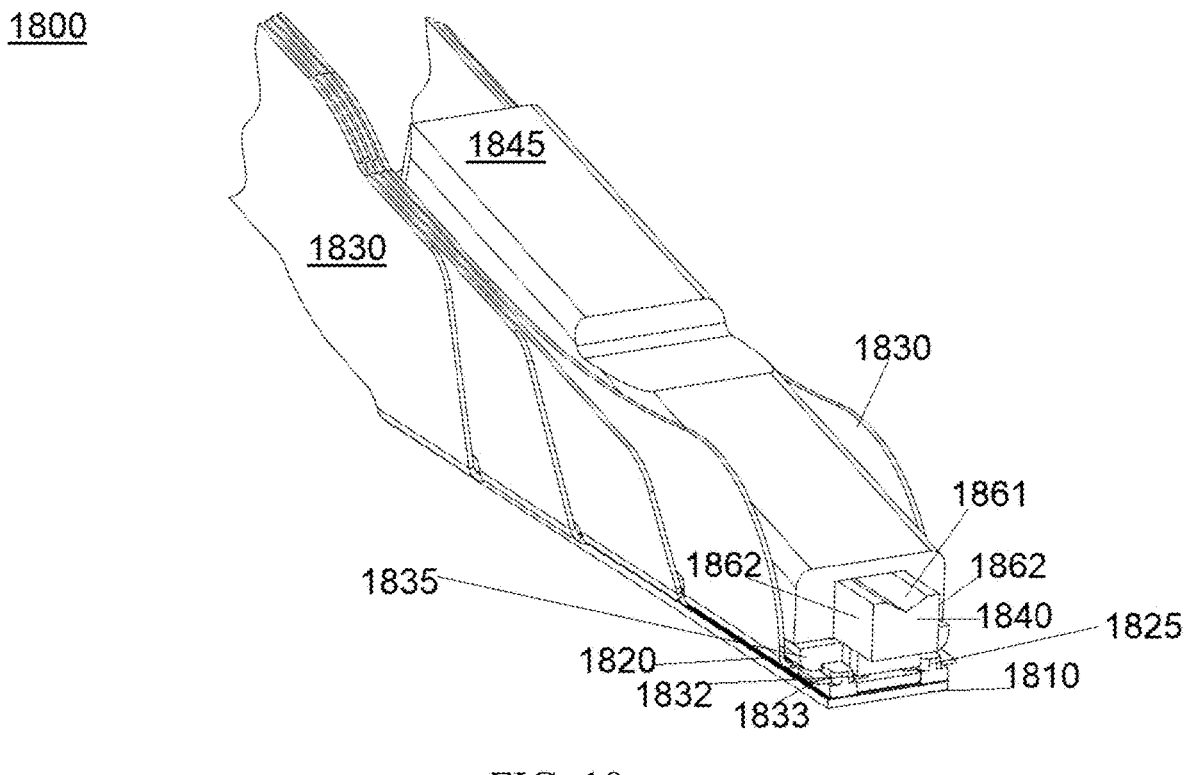
FIG. 18 provides an orthographic view of an example of a planar linear array stack described herein.
Figure 19:
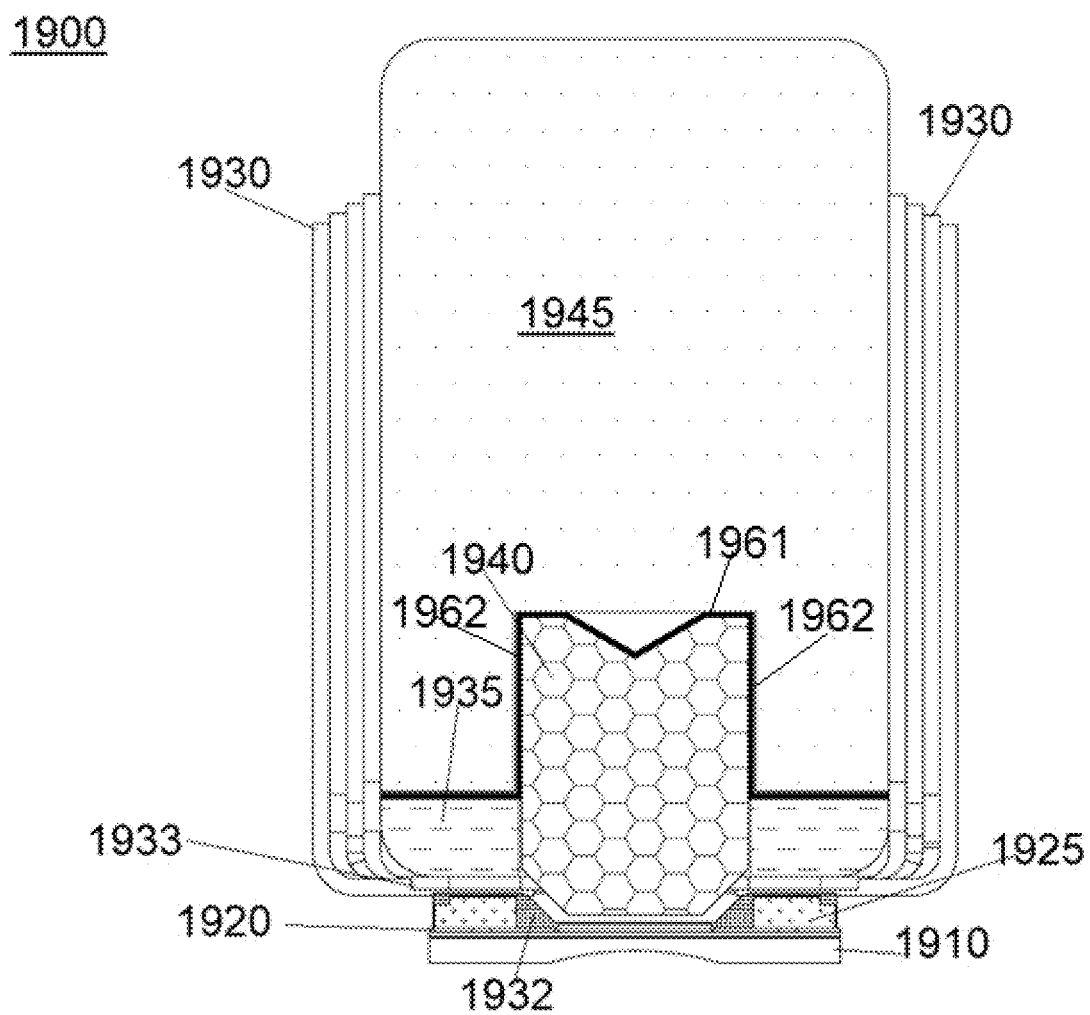
FIG. 19 provides a front view an example of a planar linear array stack described herein.

FIGS. 18 and 19 illustrate an example of a planar linear array stack 1800, 1900, including a bending spacer 1845, 1945, from two different vantage points. FIG. 18 provides an orthographic view of the planar linear array stack 1800, while FIG. 19 provides a front view of the planar linear array stack 1900. As illustrated in both figures, the planar linear array stack 1800, 1900 includes a lens layer 1810, 1910, upon which a piezoelectric layer 1820, 1920 is stacked. As discussed earlier, in certain embodiments of the planar linear array stack 1800, 1900, one or more matching layers separate the lens layer 1810, 1910, and the piezoelectric layer 1820, 1920. Although not pictured, as discussed earlier, the lens layer 1810, 1910 can include both the acoustic lens itself and a lens support structure. Similarly, the piezoelectric layer 1820, 1920 can include both a piezoelectric material and a support or frame structure that positions the piezoelectric material at substantially the same orientation as the acoustic lens along the longitudinal axis 101 (FIG. 1) and width axis 108 (FIG. 1) and on parallel planes. The piezoelectric layer 1820, 1920 can include ground trenches. An interposer frame 1825, 1925, an overmould 1832, 1932, and flex registration strips 1833, 1933 combine to secure flex circuits 1830, 1930. A flex bending frame 1835, 1935, and a backing preform 1840, 1940, guide the bending of the flex circuits 1830, 1930, while the bending spacer 1845, 1945 serves to hold the flex circuits 1830, 1930 in place after they are bent. The flex circuits 1830, 1930 are bent such that a portion of each flex circuits 1830, 1930 is substantially perpendicular to the width axis 108 (FIG. 1) axis and another portion substantially parallel to the width axis 108 (FIG. 1). The bending spacer 1845, 1945 is adjacent to a top surface 1861, 196 land at least two side surfaces 1862, 1962 of the backing preform 1840, 1940, generally surrounding parts of these surfaces. FIG. 20 depicts an example of an illustration of the bending spacer 2045 on its own so that the shape of this element can be appreciated outside the context of a planar linear array.

FIGS. 1-20 illustrate various aspects of some embodiments of planar linear arrays that can be integrated into ultrasound transducers. FIG. 21 illustrates a workflow 2100 that describes various aspects of some methods of manufacturing the planar linear arrays discussed herein and illustrated in FIGS. 1-20 and FIG. 22. The steps of the processes described in the workflow 2100 can be accomplished by an individual and/or an automated process, with the aid of various machines and manufacturing techniques. The steps provided are an example of aspects of some embodiments of the present invention and certain examples may combine, omit, and/or add one or more aspects. To manufacture a planar linear array stack for an ultrasound transducer in accordance with those described in FIGS. 1-20, form a piezoelectric layer comprising a non-metallic frame and a piezoelectric material (2110). To manufacture certain embodiments, to form the piezoelectric layer, frame the piezoelectric material with a non-metallic material on at least two sides. One can secure the non-metallic material to a portion of a perimeter of the piezoelectric material. To form the piezoelectric layer in some embodiments, one also forms one or more ground trenches in the non-metallic material, fills the one or more ground trenches with a first conductive material (e.g., silver, gold), and coats the one or more ground trenches with a second conductive material (e.g., silver, gold). The first and second materials can be the same material or different materials. For some embodiments of the planar linear array, form one or more electrodes on a surface of the piezoelectric material.

To continue the workflow 2100, form a lens support structure (2120) and bond the lens support structure to the piezoelectric layer (2130). The formed apparatus will align a lens at a central position in the stack, but the lens forming workflow will be discussed later herein. The lens support apparatus is also referred to as a lens support structure (see FIG. 2, 212 and FIG. 3, 312). Depending on the structure of the lens support apparatus (also called the lens support structure), which can be ceramic, the method of forming the structure will vary. In some examples, the lens support structure, as illustrated in FIG. 2, includes a first bar 213*a* and a second bar 213*b*, so forming the lens support structure includes orienting the first bar and the second bar to be situated on opposing sides of the lens 211. In some examples, like in FIG. 3, the lens support structure (lens support structure 312) is a frame, and forming the lens support structure includes orienting the frame around a perimeter of the curvature 314 of lens layer 310. In some examples, the lens in the planar linear array is added after all aspects of the planar linear array (illustrated in FIGS. 1, 18, and 19) except a bending spacer are formed or positioned. Thus, this workflow 2100 includes forming a lens support apparatus but not necessarily the lens, as the lens can be formed at different times in the manufacturing process.

In some examples, before the piezoelectric layer is formed, the piezoelectric material can be machined (e.g., lasered) to include one or more kerfs (see FIG. 5). Thus, before one forms the piezoelectric layer (2110), one can form one or more kerfs in the piezoelectric material, for example, by utilizing an excimer laser. The kerfs patterns one can form vary and can include, but at not limited to, cutting at least one kerf in the piezoelectric material that subdivides the piezoelectric material to maintain an aspect ratio and/or cutting a square pattern and/or a parallelogram pattern. Examples of these patterns are illustrated in FIG. 5.

Returning to FIG. 21, to continue the workflow 2100, form one or more matching layers between the lens layer and the piezoelectric layer (2140). Join the non-metallic material of the piezoelectric layer to an interposer frame (e.g., FIG. 6, 625, FIG. 7, 725) (2150). Electrically couple the interposer frame (which as a frame, includes an opening) to one or more flex circuits (see. FIG. 8) (2160). These flex circuits include traces. In some examples, utilize an overmould and/or flex registration strips (see. FIGS. 6-8) to secure the flex circuits to the interposer frame. Electrically couple the interposer frame to the traces by orienting a plurality of conductive shapes of uniform scale on a surface of the interposer frame such that the conductive shapes of uniform scale are in contact with the traces and the interposer frame (2170). In some examples, as illustrated in FIG. 11, one can dope conductive shapes of uniform scale 1150 with bonding glue and orient the conductive shapes of uniform scale 1150 between the interposer frame and the flex circuits such that the conductive shapes of uniform scale 1150 electrically connect traces (e.g., Cu fingers) 1137 on each flex circuit and traces 1127 (e.g., gold traces) on the interposer frame 1125. As discussed earlier, in this example each conductive shapes of uniform scale conductive shapes of uniform scale 1150 is comprised of a dielectric material (e.g., glass, polymer) and coated uniformly with the conductive material (e.g., copper, gold, silver, titanium, etc.).

Once the flexes are secured to the interposer frame and electrical connectivity has been established via the conductive shapes of uniform scale, orient a flex bending frame (with an opening) substantially parallel to a first portion of the one or more flex circuits, such that a second portion of each flex circuit of the one or more flex circuits extends beyond an outer boundary of the interposer frame. It is around this outer boundary that the second portion will be bent (2180). FIG. 12-14 include examples of the flex bending frame 1235, 1345, 1435 and its orientation within a planar linear stack during assembly of the stack. The bending of the flex circuits is also guided by a bending spacer. To enable the bending, orient a backing preform such that the bending spacer extends through openings in the interposer frame and the flex bending frame (see, e.g., FIGS. 14-16) (2190).

As discussed earlier, a lens can be formed at different points in the workflow 2100. However, one can form a lens in the lens support structure. Specifically, once the array is completed to a stage where the flex circuits are attached and the array is backed to secure the structure (e.g., the backing preform), one can insert a lens into the lens support structure and create a curvature in the lens by rotating a rod and parallel rubbing a surface of the lens to a certain depth. Alternatively, the lens can be added at the time the lens layer is added to the stack, but the curvature is created at this later time, after the backing preform has been attached. Thus, once the preform is attached, one can add and/or implement a curvature in the lens (2192).

Figure 22:
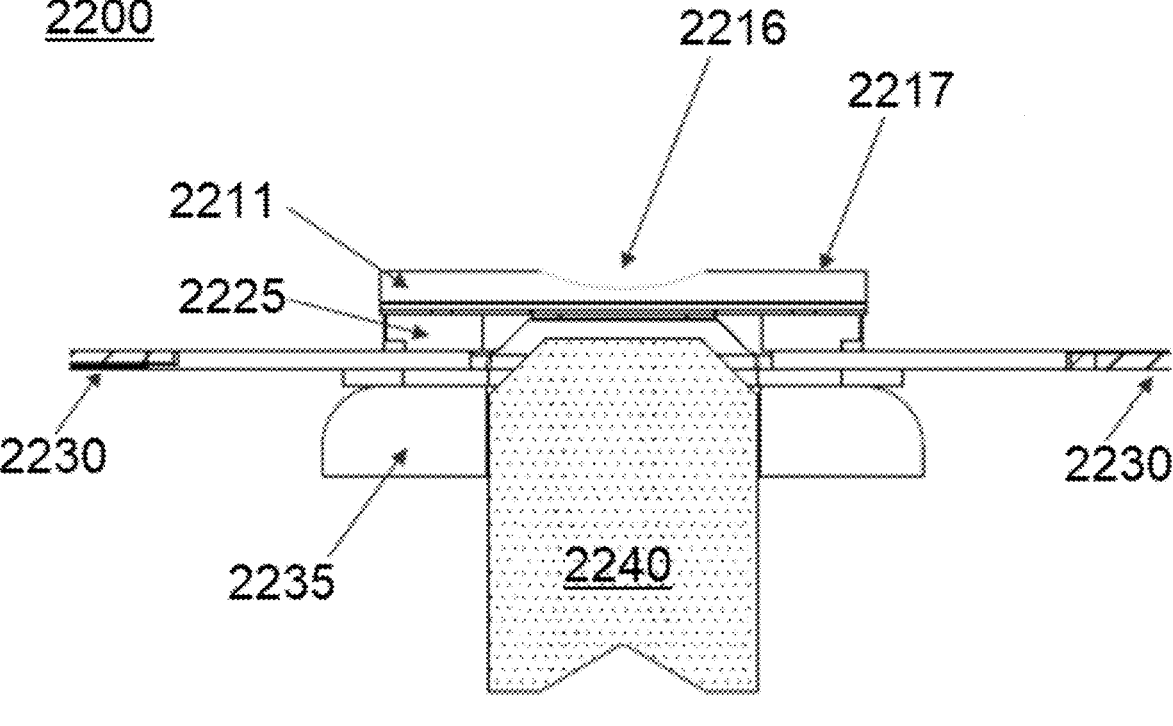
FIG. 22 illustrates an example of a technique for forming a lens utilized in a transducer comprising an example of the planar linear array stack described herein.

FIG. 22 illustrates an example of a technique for forming a lens utilized in a transducer comprising an example of the planar linear array stack described herein. The resultant transducer will focus an ultrasound beam to a certain depth of the imaging field. The curvature of the lens 2216 provides this focus. In order to form the curvature of the lens, one assembles a portion of a planar linear array stack 2200, including a lens layer, which in this non-limiting example is just an acoustic lens 2211, an interposer frame 2225, one or more flexes 2230, a flex bending frame 2235, and a backing preform 2240. One completes assembly of the planar linear array stack 2200 through attaching the one or more flexes 2230 and backing the structure with the backing preform 2240 (e.g., FIG. 21, 2110,-2910). One places the planar linear array 2200 is a fixture, orienting the acoustic lens 2211 upwards (this is the opposite vertical orientation of this element when compared to FIG. 1). Create a curvature 2216 on the acoustic lens 2211 by rotating a rod and parallel rubbing the exposed upper surface 2217 to a certain depth.

Returning to FIG. 21, to further enable the bending and to support the flex circuits once they are in a bent position, orient a bending spacer (e.g., FIG. 1, bender spacer 145, FIG. 19, bending spacer 1945, and FIG. 20, bending spacer 2045) above an upper surface of the backing preform and on a portion of two sides of the backing preform, where the two sides of the backing preform are parallel to the upper surface of the backing preform (2194). Bend the flexes around outer boundaries of the flex bending frame and the bending spacer (2195). The resulting planar linear array can be placed in a housing for use in an ultrasound probe.

Advantages of the examples of linear planar arrays described herein and the manufacturing process for these examples include, but are not limited to: simplifying manufacturing tools, eliminating lengthy manufacturing processes, reducing manufacturing difficulties, reducing dependency on operator skills, reducing failure rates, and decreasing reduction costs. The arrays described herein, when integrated into ultrasound transducers, provide the advantages listed above without comprising yield and thus provide substantially the same and/or improved fit, form, and function when compared to existing systems.

Embodiments of the present invention include an ultrasound transducer and methods of manufacturing and using this ultrasound transducer. In some examples, the ultrasound transducer includes a planar linear array stack. The planar linear array stack can include a lens layer comprising an acoustic lens and a lens support structure. A portion of the acoustic lens is secured to the lens support structure. The planar linear array stack can also include a piezoelectric layer comprising a non-metallic frame and a piezoelectric material, the non-metallic frame surrounding the piezoelectric material on at least two sides, the non-metallic frame coupled to a portion of the lens support structure such that the acoustic lens and the non-metallic frame are oriented substantially parallel to each other. The ultrasound transducer can also include an interposer frame to position one or more flex circuits, where the interposer frame is coupled to the non-metallic frame via a conductive element in the non-metallic frame and to the one or more flex circuits. The one or more flex circuits are also included in this ultrasound transducer.

In some examples of the ultrasound transducer, the one or more flex circuits and the interposer frame are electrically coupled to a ground electrode.

In some examples of the ultrasound transducer, the lens support structure comprises a first bar and a second bar. The first bar and the second bar are situated on opposing sides of the acoustic lens.

In some examples of the ultrasound transducer, the lens support structure comprises a frame that surrounds a rectangular perimeter of the acoustic lens.

In some examples of the ultrasound transducer, the lens support structure comprises ceramic.

In some examples of the ultrasound transducer, the acoustic lens comprises a curvature, where the curvature having minima on a line, the line parallel to the piezoelectric material in the planar linear array stack.

In some examples of the ultrasound transducer, the acoustic lens comprises a dielectric material.

In some examples of the ultrasound transducer, the piezoelectric material comprises one or more kerfs; the kerfs comprise a pattern.

In some examples of the ultrasound transducer, the one or more kerfs comprise a line subdividing the dielectric material to maintain an aspect ratio.

In some examples of the ultrasound transducer, the pattern is selected from the group consisting of: a square pattern, and a parallelogram pattern.

In some examples of the ultrasound transducer, the non-metallic frame comprises one or more ground trenches.

In some examples of the ultrasound transducer, at least one of the one or more ground trenches is filled with a first conductive material and based on being filled, coated with a second conductive material.

In some examples of the ultrasound transducer, the non-metallic frame surrounding the piezoelectric material is bonded to an outer boundary of the piezoelectric material with a glue.

In some examples of the ultrasound transducer, the ultrasound transducer includes one or more matching layers between the lens layer and the piezoelectric layer.

In some examples of the ultrasound transducer, the piezoelectric layer comprises electrodes on a surface proximate to the one or more matching layers.

In some examples of the ultrasound transducer, the interposer frame is electrically coupled to the one or more flex circuits via a plurality of conductive shapes of uniform scale coated with a conductive material.

In some examples of the ultrasound transducer, the plurality of conductive shapes of uniform scale conducts an electrical signal from a surface of the interposer frame in contact with the plurality of conductive shapes of uniform scale to traces on a surface of the one or more flex circuits in contact with the plurality of conductive shapes of uniform scale.

In some examples of the ultrasound transducer, each conductive shape of uniform scale of the plurality of conductive shapes of uniform scale is comprised of a dielectric material.

In some examples of the ultrasound transducer, each conductive shape of uniform scale of the plurality of conductive shapes of uniform scale is coated with the conductive material.

In some examples of the ultrasound transducer, the surface of the interposer frame in contact with the plurality of conductive shapes of uniform scale comprises one or more conductive traces.

In some examples of the ultrasound transducer, the electrical connection via the plurality of conductive shapes of uniform scale coated with the conductive material forms a vertical electrical connection between the interposer frame and the one or more conductive traces, which are oriented on parallel planes.

In some examples of the ultrasound transducer, the ultrasound transducer includes a frame positioned substantially parallel to a first portion of the one or more flex circuits, such that a second portion of each flex circuit of the one or more flex circuits is bent substantially perpendicular to a surface of the frame perpendicular to the planar linear array stack such that the frame and the lens layer are on parallel horizontal planes.

In some examples of the ultrasound transducer, the ultrasound transducer includes one or more flex registration strips. Each flex registration strip is positioned between the interposer frame and the frame positioned substantially parallel to a first portion of the one or more flex circuits.

In some examples of the ultrasound transducer, each flex circuit of the one or more flex circuits is attached to a flex registration strip of the one or more flex registration strips.

In some examples of the ultrasound transducer, the frame positioned substantially parallel to the first portion of the one or more flex circuits comprises a first cavity and the interposer frame comprises a second cavity. In this example, the ultrasound transducer also includes a backing preform extending through the first cavity and the second cavity in contact with a portion of the one or more flex circuits.

In some examples of the ultrasound transducer, the backing preform is coated with a conductive tape.

In some examples of the ultrasound transducer, the transducer includes a bending spacer. The bending spacer is positioned above the backing preform such that the second portion of each flex circuit of the one or more flex circuits is substantially parallel to a surface of the bending spacer perpendicular to the planar linear array stack.

In some examples of the ultrasound transducer, the non-metallic frame positions the piezoelectric material in a central position relative to an elevation and width of the planar linear array stack.

In some examples of the ultrasound transducer, the transducer includes an overmould which secures the one or more flex circuits to the interposer frame.

In some examples of the ultrasound transducer, the overmould includes electrodes on at least one surface.

In some examples of the ultrasound transducer, the ultrasound transducer includes a planar linear array stack that includes a lens layer comprising a lens, one or more matching layers between the lens layer and a piezoelectric layer, and the piezoelectric layer comprising a non-metallic frame and a piezoelectric material, the non-metallic frame surrounding the piezoelectric material on at least two sides. The transducer can also include an interposer frame to position one or more flex circuits. The interposer frame is coupled to the non-metallic frame via a conductive element in the non-metallic frame and to the one or more flex circuits. The transducer also includes the one or more flex circuits.

In some examples of the ultrasound transducer, the ultrasound transducer includes a planar linear array stack, comprising: a lens layer comprising a lens, and a piezoelectric layer comprising a non-metallic frame and a piezoelectric material, the non-metallic frame surrounding the piezoelectric material on at least two sides, the non-metallic frame coupled to a portion of the lens layer. The transducer can also include an interposer frame to position one or more flex circuits, where the interposer frame is coupled to the non-metallic frame via a conductive element in the non-metallic frame and to the one or more flex circuits. The transducer can also include the one or more flex circuits.

In some examples of a method of manufacturing a planar linear array stack for an ultrasound transducer, the method includes forming a piezoelectric layer comprising a non-metallic material and a piezoelectric material, where the forming comprises framing the piezoelectric material with the non-metallic material on at least two sides. The method can also include forming a lens support structure, where the lens support structure orients an acoustic lens at a central position relative to a width and elevation of the planar linear array stack. The method can also include bonding the lens support structure to the piezoelectric layer, such that the lens support structure and the piezoelectric layer are parallel relative to the width and the elevation.

In some examples of the method, the lens support structure comprises a first bar and a second bar and forming the lens support structure comprises: orienting the first bar and the second bar to be situated on opposing sides of the lens.

In some examples of the method, the lens support structure comprises a frame, and forming the lens support structure comprises: orienting the frame around a perimeter of the lens.

In some examples of the method, the lens support structure comprises ceramic.

In some examples of the method, the method includes forming one or more kerfs in the piezoelectric material.

In some examples of the method, the forming the one or more kerfs comprises cutting at least one kerf in the piezoelectric material that subdivides the piezoelectric material to maintain an aspect ratio.

In some examples of the method, the forming the one or more kerfs comprises cutting a pattern of kerfs into the piezoelectric material.

In some examples of the method, the pattern is selected from the group consisting of a square pattern and a parallelogram pattern.

In some examples of the method, the method includes forming one or more ground trenches in the non-metallic material.

In some examples of the method, the method includes filling the one or more ground trenches with a first conductive material. The method can also include coating the one or more ground trenches with a second conductive material.

In some examples of the method, the forming the piezoelectric layer further comprises securing the non-metallic material to a portion of a perimeter of the piezoelectric material.

In some examples of the method, the method includes forming one or more matching layers between the lens layer and the piezoelectric layer.

In some examples of the method, the forming the piezoelectric layer further comprises: forming one or more electrodes on a surface of the piezoelectric material.

In some examples of the method, the method includes joining the non-metallic material of the piezoelectric layer to an interposer frame.

In some examples of the method, the method includes electrically coupling the interposer frame to one or more flex circuits, where a surface of each of the one or more flex circuits comprises a trace, where the interposer frame comprises a first opening, where the electrically coupling comprises securing the one or more flex circuits to the interposer frame with an overmould, and where a surface of the overmould comprises one or more electrodes.

In some examples of the method, the electrically coupling comprises orienting a plurality of conductive shapes of uniform scale on a surface of the interposer frame. The method can also include electrically coupling the interposer frame to the traces by coupling the traces to the plurality of conductive shapes of uniform scale.

In some examples of the method, each conductive shape of uniform scale of the plurality of conductive shapes of uniform scale comprises a dielectric material coated with a conductive material.

In some examples of the method, the method includes orienting a flex bending frame substantially parallel to a first portion of the one or more flex circuits, such that a second portion of each flex circuit of the one or more flex circuits extends beyond an outer boundary of the interposer frame, where the flex bending frame comprises a second opening.

In some examples of the method, the electrically coupling the interposer frame to one or more flex circuits further comprises: affixing each of the one or more flex circuits to a registration strip of a plurality of registration strips; and orienting each flex registration strip of the plurality such that it is positioned between the interposer frame and the flex bending frame.

In some examples of the method, the method includes orienting a backing preform, where the backing preform is in contact with a given portion of the one or more flexes based on extending through the first opening and the second opening.

In some examples of the method, the method includes forming the lens in the lens support structure.

In some examples of the method, the method includes bending the second portion of each flex circuit of the one or more flex circuits to orient the second portion of each flex circuit substantially perpendicular to a surface of the flex bending frame.

In some examples of the method, the method includes orienting a spacer above an upper surface of the backing preform and on a portion of two sides of the backing preform, wherein the two sides of the backing preform are parallel to an upper surface of the backing preform.

In some examples of the method, the method includes depositing copper shielding on an upper surface of the backing preform.

In some examples of the method, the method includes utilizing the non-metallic material to position piezoelectric material in a central position in the planar linear array stack relative to the elevation and the width.

Figure 24:
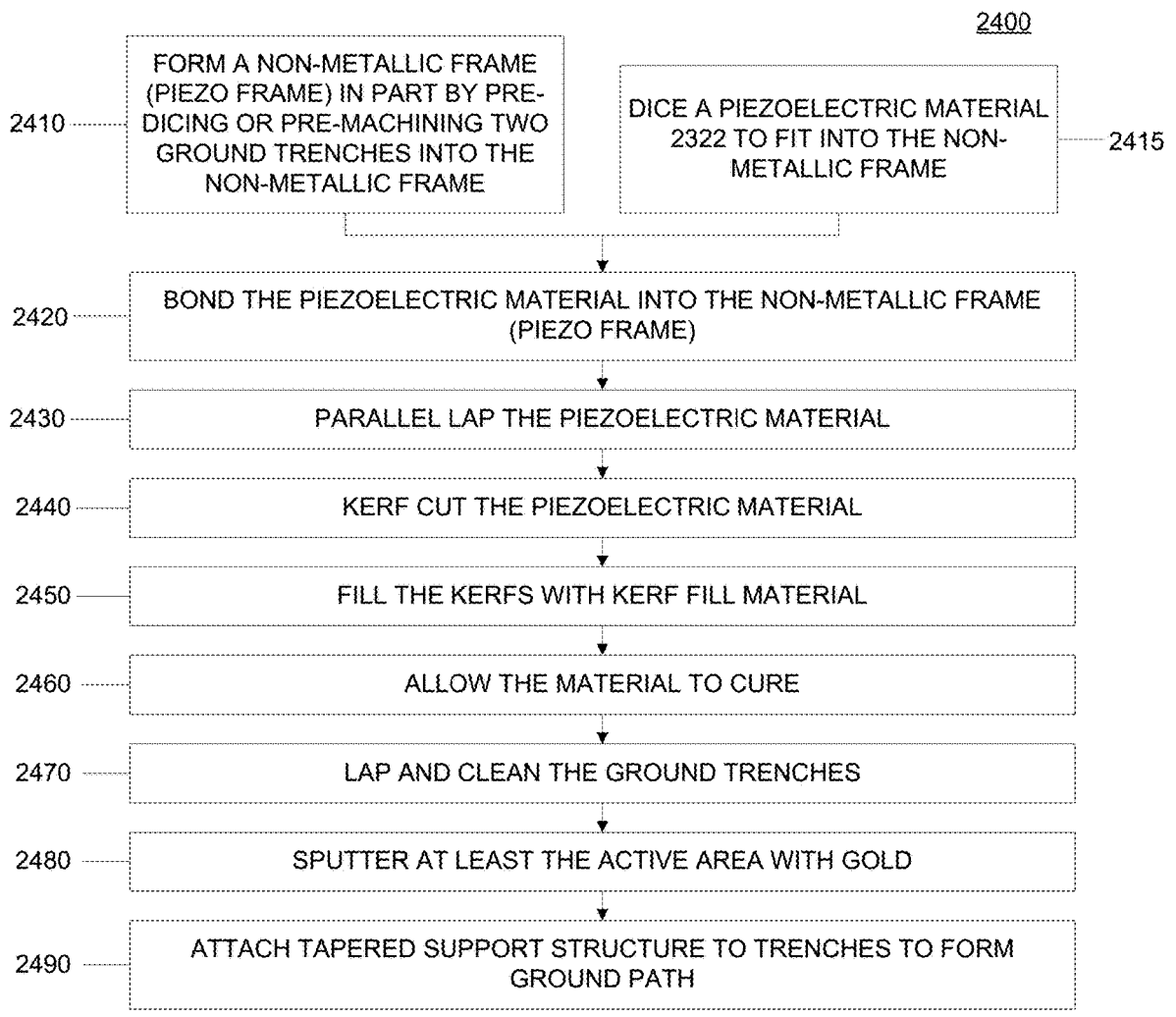
FIG. 24 illustrates a workflow that describes various aspects of some methods of manufacturing the piezoelectric layer described in FIGS. 23 and 25.

FIGS. 23 and 24 depict various aspects in a non-limiting method 2300, 2400 of forming a piezoelectric layer 2320 (e.g., FIG. 4, 420) from the top view. While FIG. 23 depicts the evolution of the piezoelectric layer 2320 itself through a manufacturing process, FIG. 24 illustrates a workflow that describes various aspects of some methods of forming the piezoelectric layer 2320.

Turning to FIG. 23, at the conclusion of its formation, the piezoelectric layer 2320 includes a non-metallic frame 2321, which is also referred to herein as a piezo frame, which can be comprised of an insulating material, including but not limited to, ceramic. The non-metallic frame 2321 can be referred to as a piezo frame because it frames and positions piezoelectric material 2322 within a stack in a transducer. The term piezo frame does not refer to the material which the frame is constructed from. Rather, the non-metallic frame 2321 or piezo frame is formed from a material, including but not limited to, ceramic, the material of the non-metallic frame 2321 (or piezo frame) being selected for its hardness, high melting point, low thermal expansion, and/or good chemical resistance.

The non-metallic frame 2321 encloses a piezoelectric material 2322 (e.g., PZT, PZT/SX, etc.). In the context of this example, the non-metallic frame 2321 serves at least one of four functions: 1) it centers the piezoelectric material 2322 along the longitudinal axis 101 (FIG. 1) and the width axis 108 (FIG. 1) of the planar linear array 100 (FIG. 1); 2) it defines the elevation (e.g., FIG. 1, 101) of the planar linear array 100 (FIG. 1); 3) it includes ground trenches 2323 to bring ground connections from the front to the back of the piezoelectric layer 2320 (forming part of a return signal path); and 4) it reduces the stress on the piezoelectric layer 2320 material during the manufacturing process 2300, 2400.

The piezoelectric layer 2320 can serve as a pure 1-3 composite used in a transducer, including an ultra-high frequency transducer that operates with ultrasound above 15 MHz. As noted earlier, the transducers described herein can operate at frequencies that span low to ultra-high frequencies. The non-metallic frame 2321 holds the piezoelectric material 2322 in place such that the piezoelectric material 2322 is centered on the width axis 108 (FIG. 1) and longitudinal axis 101 (FIG. 1). The non-metallic frame 2321 defines the elevation width by controlling the width of the central opening (also referred to as an active surface, based on positioning according to the width axis 108 (FIG. 1) and longitudinal axis 101 (FIG. 1) (into which the piezoelectric material 2322 is placed). For example, the non-metallic frame 2321 can maintain the consistency of the elevation width. The non-metallic frame 2321 also provides a ground path from the piezoelectric material 2322 to the flex circuits (e.g., FIG. 1, 130) via ground trenches 2323. In an example, the ground trenches include a series of holes (e.g., round and/or rectangular holes). The piezoelectric layer 2320 is illustrated in the context of the planar linear array 100 of FIG. 1, but it can be utilized in additional devices, replacing the piezoelectric layer in these devices. As noted above, the term trench is used herein to represent different types of fissures in a material. In FIG. 4, the trenches are more traditionally understood literal ground trenches 423, but in this example, the ground trenches 2323 can be more accurately described as grooves. Because the structure of this element can be flexible and vary based on the resultant transducer, the term "trench" is being used in this generic manner. The ground path and elements therein, such as the trenches, bring ground connections from one side to an opposite side of the piezoelectric layer 2320 (forming part of a return signal path). In some examples, ground trenches 423 include a series of holes, including but not limited to, round and/or rectangular holes. The trench brings the ground connection from one side to the opposite side.

Although the transducers manufactured in accordance with the methods described herein can operate at high frequencies and ultrahigh frequencies, in some examples, the manufacturing methods described herein can be utilized to manufacture transducers that operate at a large range of frequencies. For example, certain methods described herein can be utilized to manufacture he arrays that can cover at least covers the operating center frequency from −1 MHz to −70 MHz.

Referring to FIGS. 23 and 24, to manufacture 2300, 2400 the piezoelectric layer 2320, one individually prepares both the non-metallic frame 2321 and the piezoelectric material 2322 before they are united into the piezoelectric layer 2320. To prepare the non-metallic frame 2321, form a non-metallic frame 2321 (piezo frame) in part by pre-dicing or pre-machining two (e.g., two or more) ground trenches 2323 into the non-metallic frame 2321 (2410). To prepare the piezo-electric material 2322, dice a piezoelectric material 2322 to fit into the non-metallic frame 2321 (2415). To set the shape, size, and thickness of the piezoelectric material 2322, one can pre-dice the material itself into sections or array ele-ments of a desired shape, size, and thickness for the desired use. Because the piezoelectric material 2322 is positioned in the piezoelectric layer 2320 in a frame that is not made of piezoelectric material, the amount of piezoelectric material 2322 in the piezoelectric layer 2320 is reduced to a mini-mum length that covers an active area. This configuration of the piezoelectric layer 2320 (e.g., the inclusion of the non-metallic frame 2321) represents a cost savings in the manufacturing process. In one non-limiting example, the piezoelectric material 2322 is cut to a precise size of 46.0 mm×2.8 mm, with the elevation width of 2.4 mm. Dicing the piezoelectric material 2322 only to a size to cover the active area is a departure from the earlier method where one diced a piezoelectric material 2322 to a size larger than the active area and then treated only an area that would cover the active area, leaving excess around the edges in which to form ground connections. Once the piezoelectric material 2322 and the non-metallic frame 2321 (with the ground trenches 2323, which can be formed using a laser or otherwise pre-machined), one can bond 2328 the piezoelectric material 2322 (e.g., PZT) into the non-metallic frame 2321 (e.g., the piezo frame) (2420). The bond 2328 can be comprised of a bonding agent such as glue and/or epoxy that will not denature during use of the resultant transducer.

Once the piezoelectric material 2322 has been bonded 2328 into the non-metallic frame 2321 (2420), one can remove any excess adhesive and/or residue and thin the piezoelectric material 2322 to a desired thickness, by eve-ning out the surface of the piezoelectric material 2322 (2430). To even out the surface, various techniques can be utilized, including but not limited to, lapping (including parallel lapping), grinding, shaving, and/or machining. One can then kerf cut 2327 the piezoelectric material 2322 (2440). Various examples of kerf cuts are illustrated herein in FIG. 5. However, in some examples, rather than cutting both short and long cuts, one can cut kerfs in the piezoelec-tric material 2322 only in a single direction (e.g., single cuts), rather than the short/long kerf cuts which are standard in some existing transducers. Cutting the kerfs in this manner enables one to use different types of materials to fill the kerfs, including materials that cure more quickly. Thus, the examples depicted in FIG. 23 can utilize a greater variety of kerf fill materials because the curing can occur more quickly and still produce a usable piezoelectric layer 2320. The curing process can be slower in some existing high frequency transducers because utilizing a piezoelectric layer 2320 with a non-metallic frame 2321 adds extra stability to the piezoelectric layer 2320 so the piezoelectric material 2322 is protected and damages prevented by the longer curing time are less likely.

As aforementioned, one fills the kerfs with kerf fill material 2325 (2450). Various types of materials can be used to fill kerfs 2327 in a piezoelectric layer 2320, including but not limited to a liquid or a solid, such as, for example, a polymer. A kerf fill 2325 that cures more quickly can be utilized in these examples. To maintain the structural integ-rity of the piezoelectric layer 2320 and the resultant trans-ducer, in some examples, one allows the kerf fill to cure for no more than a day. Existing transducers that do not utilize a non-metallic frame 2321 and instead include a piezoelec-tric layer formed from a piezoelectric material, are generally cured for at least 5 days. Thus, incorporating a piezoelectric layer with a non-metallic frame element can decrease manu-facturing time by reducing the time utilized to cure material filling the kerfs in the piezoelectric material. One allows the material to cure (2460) and when the curing is complete (e.g., a day has elapsed), as illustrated in FIGS. 23 and 24, one can lap and clean the ground trenches 2323 (e.g., to remove any unwanted fill material which may have migrated there during the curing process and to bring the piezoelectric layer 2320 to a desired thickness (2470). Referring to FIG. 9, piezoelectric layer 920 illustrates a desired thickness of the piezoelectric layer 2324 (FIG. 23). In some examples, the piezoelectric layer 2320 can be lapped down to an elevation of −100 microns. Because the kerf material cured for less time compared to conventional methods, the lapping process is simplified. After lapping, sputter the surface of the piezoelectric layer 2320 with gold 2329 such that the gold 2329 covers the piezoelectric material 2322 (2480). Risks of the sputtering adversely affecting the piezoelectric layer 2320 because rather than sputter the entirety of the piezo-electric layer, as is done in some existing methods, one can target the sputtering to cover the active area (e.g., the piezoelectric material 2322).

Utilizing the configuration of the piezoelectric layer 2320 introduces various advantages to the manufacturing process and to the integrity of the resultant ultrasound transducer. For example, the non-metallic frame 2321 provides addi-tional structure to an ultrasound transducer, preventing warping of the piezoelectric material 2322 during use. Additionally, the non-metallic frame 2321 also protects the piezoelectric material 2322 during manufacturing because, as illustrated in FIG. 24, when constructing the piezoelectric layer 2320, one forms ground trenches 2323 in the piezo-electric layer 2320. In existing transducer stacks, one forms trenches in the piezoelectric material, itself, specifically, piezoelectric material surrounding the portion of the piezo-electric layer of the active surface. However, because the piezoelectric material is continuous, lasering trenches in part of the piezoelectric layer could impact the structural integ-rity of the entire layer. Thus, by pre-machining the trenches, the piezoelectric material is not exposed to the heat involved in forming trenches and will not warp, burn, or otherwise denature as a result of the heat. For example, piezoelectric layers can often chip because the material was denatured by this heat, but the pre-machined non-metallic frame 2321 protects the piezoelectric layer 2320 as a whole and the piezoelectric material 2322 from chipping. The configura-tion of the piezoelectric layer 2320 also decreases pitch error or walk off Because one machines the ground trenches 2323 in the non-metallic frame 2321 before gluing the piezoelec-tric material 2322 into the non-metallic frame 2321, the piezoelectric material 2322 is less likely to be warped through a heating process that would result in pitch error or walk off The heat can also cause pitch error or walk off of kerfs.

In some existing piezoelectric layers, one machines ground trenches or ground slots (sometimes multiple ground slots) into a portion of the piezoelectric material that does not cover the active surface, but this is part of the same piece of piezoelectric material that does cover the active surface. When grounds for the piezoelectric layers are, for example, drilled with a high power laser process, the whole layer is exposed to the heat and the dimensions can change, meaning that the slots are no longer at an optimal distance from each other. Some existing piezoelectric layers include multiple ground slots while some examples of the piezoelectric layer 2320 described herein include only two ground trenches. In one example, the piezoelectric layer 2320 includes a single ground trench. Having fewer ground vias also decreases the likelihood of pitch error or walk off Drilling slots or any type of channels directly into a piezoelectric material can also create stress points in that material. Because the methods illustrated in FIGS. 23 and 24 avoid this step, the integrity of the piezoelectric material is preserved.

Returning to FIGS. 23 and 24, to form a ground path, which utilizes the ground trenches 2323, one can pre-fill the trenches with a conductive material such as silver-filled epoxy prior to attaching a tapered structure 2343 over the filled ground trenches 2323, forming the ground path (2490). This filling ensures an electrical continuity of ground to the tapered support structure 2343. In certain of the examples herein, a support structure utilized in the disclosed transducers is illustrated as a tapered support due to its cross sectional geometry. However, this is merely one type of geometric configuration for a support structure, as any shape, tapered or otherwise, could be utilized in various examples herein provided that it provides the advantages of the illustrated examples. Thus, although FIG. 23, for example, illustrates a tapered support structure 2343, additional shaped support structures can be integrated into the examples herein.

Figure 25:
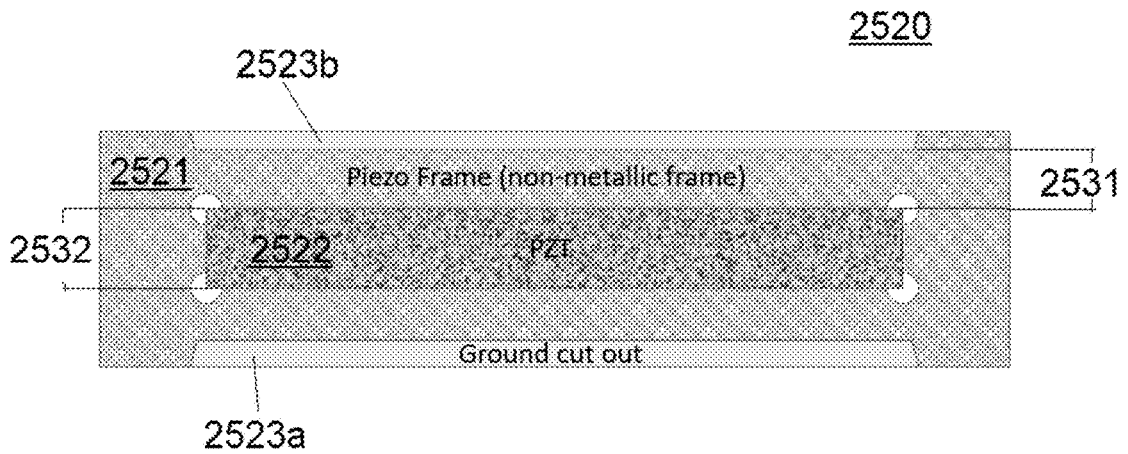
FIG. 25 depicts an example of a piezoelectric layer which can be integrated into examples of the planar linear array stacks described herein.

Referring to the non-limiting example illustrated in FIG. 23, the tapered (in this example) structure 2343 can be attached with a bonding agent and will act as a ground path, sitting on the ground trenches 2323, which are open slots. Because there are only two ground trenches 2323, in this non-limiting example, aligning the tapered structure 2343 to act as the ground path is simpler than in some existing piezoelectric layers, which can include multiple slots in place of these two ground trenches 2323 (illustrated in FIG. 25 as a top trench 2523a and a bottom trench 2523b). This tapered support and configuration of ground trenches 2323 is provided merely as an example of a possible configuration. In FIG. 25, both the top trench 2523a and a bottom trench 2523b ground the transducer but in some examples, the top trench 2523a is slightly narrower than the bottom trench 2523b. In other examples, the bottom trench 2523b can be narrower than the top trench 2523a. As illustrated in FIG. 23 and discussed earlier, the non-metallic frame 2321 can be created (e.g., machined, molded, cast, 3D printed, etc.) in a variety of patterns and combined with different types of supports to create a ground path. The tapered support 2343 of FIG. 23 is provided to illustrate the flexibility of the piezoelectric layer 2320 and the ease with which it can be integrated into a known configuration. When compared with examples of transducers herein that include an interposer frame, the tapered support 2343 can be understood as a replacement or substitute for an interposer frame (e.g., FIG. 9, 925) because like an interposer frame, a tapered support 2343 provides rigidity and a ground path and a support structure on to which one can bond overmould (e.g., FIG. 932).

FIG. 25 is a detailed view of a piezoelectric layer 2520, which is an example of the piezoelectric layers illustrated in FIGS. 4 and 23. As illustrated in FIG. 25, a piezoelectric layer 2520 of a transducer can include a non-metallic frame 2521 (piezo frame) and a piezoelectric material 2522 (depicted in FIG. 25 as PZT). The non-metallic frame 2521 (piezo frame) includes two ground trenches 2523a and 2523b (collectively 2523), also referred to as cutouts, as they were pre-machined before the piezoelectric layer 2520 was assembled. In this non-limiting example, the ground trenches 2523 (cutouts) are of different widths but approximately 0.4 mm to an edge of the piezoelectric layer 2520. The piezo margin 2531 and the elevation/opining width 2532 are also designated in this illustration.

Figure 26:
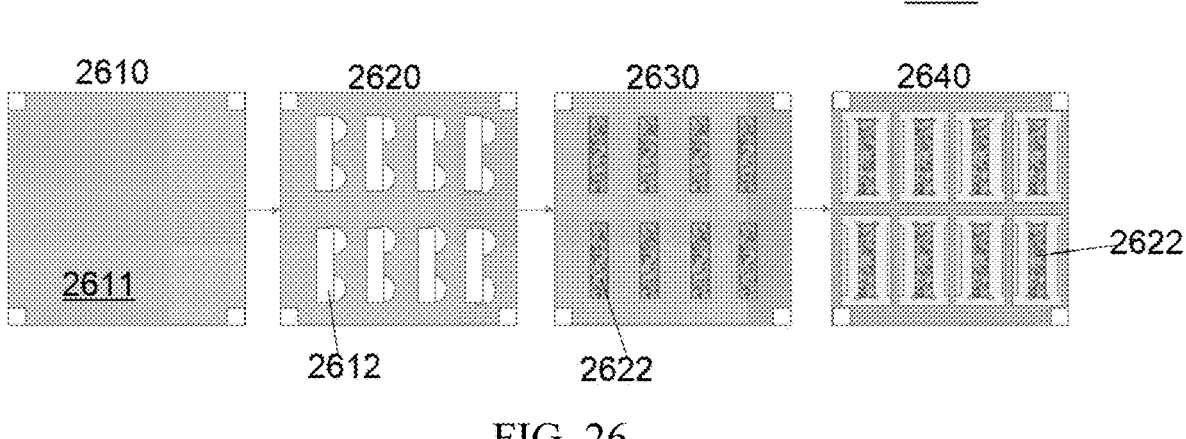
FIG. 26 illustrates an example of a technique for forming a plurality of piezoelectric layers for use in transducers that can comprise examples of the planar linear array stack described herein.

When manufacturing the piezoelectric layer 2320, 2520, one can build the layers in batches, which is an advantage over certain existing piezoelectric layers, which are individually produced. FIG. 26 illustrates various steps in a process 2600 for producing a batch of piezoelectric layers (e.g., piezoelectric layer 2320, 2520). This example shows a batch of eight piezoelectric layers, however, this example is merely provided to illustrate this process and depending upon the machinery and/or space available, batches of different sizes can be constructed. In some examples, the process can be performed by a lapping machine.

Figure 27:
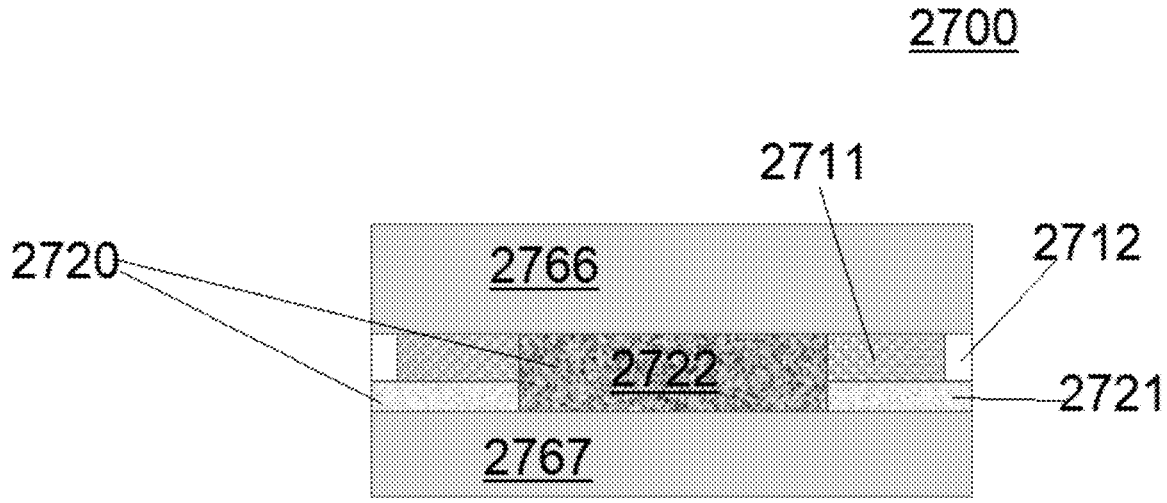
FIG. 27 illustrates an example of a cross section that is a part of the process illustrated in FIG. 26.

FIG. 26 illustrates a workflow 2600 that includes elements of the workflow 2600 to assist in illustrating aspects of the workflow. As illustrated in FIG. 26, the workflow 2600 commences by placing foil or sheet material 2611 over a surface, including but not limited to a plate (not pictured) (2610). Examples of the foil 2611 include gold, silver, aluminum, plastic, and the like. One can place individual stencils 2612 on the foil 2611 (at piezoelectric layer (e.g., piezoelectric layer 2320, 2520) (2620). The stencils 2612 pictured are just an example of a shape of a stencil that can be used to guide the placement of the piezoelectric material 2622 portion of the resultant piezoelectric layer (e.g., piezoelectric layer 2320, 2520). These stencils 2612 (which provide a non-limiting option) have openings to enable targeted placement of a bonding agent, including but not limited to, cyanoacrylate. One bonds the pre-diced piezoelectric material 2622 onto the foil 2611, using the stencils 2612 as placement guides (2630). Once the piezoelectric material 2622 is in place, one can bond the non-metallic frame 2621 to the piezoelectric material 2622 (or vice versa) (2640). To hold the resultant piezoelectric layers (e.g., piezoelectric layer 2320, 2520) parallel while the bonding agent cures, a second plate (not pictured) can be placed on top of the assembly. Once the bond is secure (e.g., if glue is used as a bonding agent, once it has cured), one can remove the plates, the excess bonding agent, and the foil 2611, leaving the piezoelectric layer (e.g., piezoelectric layer 2320, 2520) (before it is kerf cut, filled, and/or sputtered). FIG. 27 provides a cross section 2700 of a single piezoelectric layer 2720 situated between a first plate 2766 and a second plate 2767. Visible in the cross section 2700 is the foil 2711, stencil 2712, the piezoelectric material 2722, and the non-metallic frame 2721.

Figure 28:
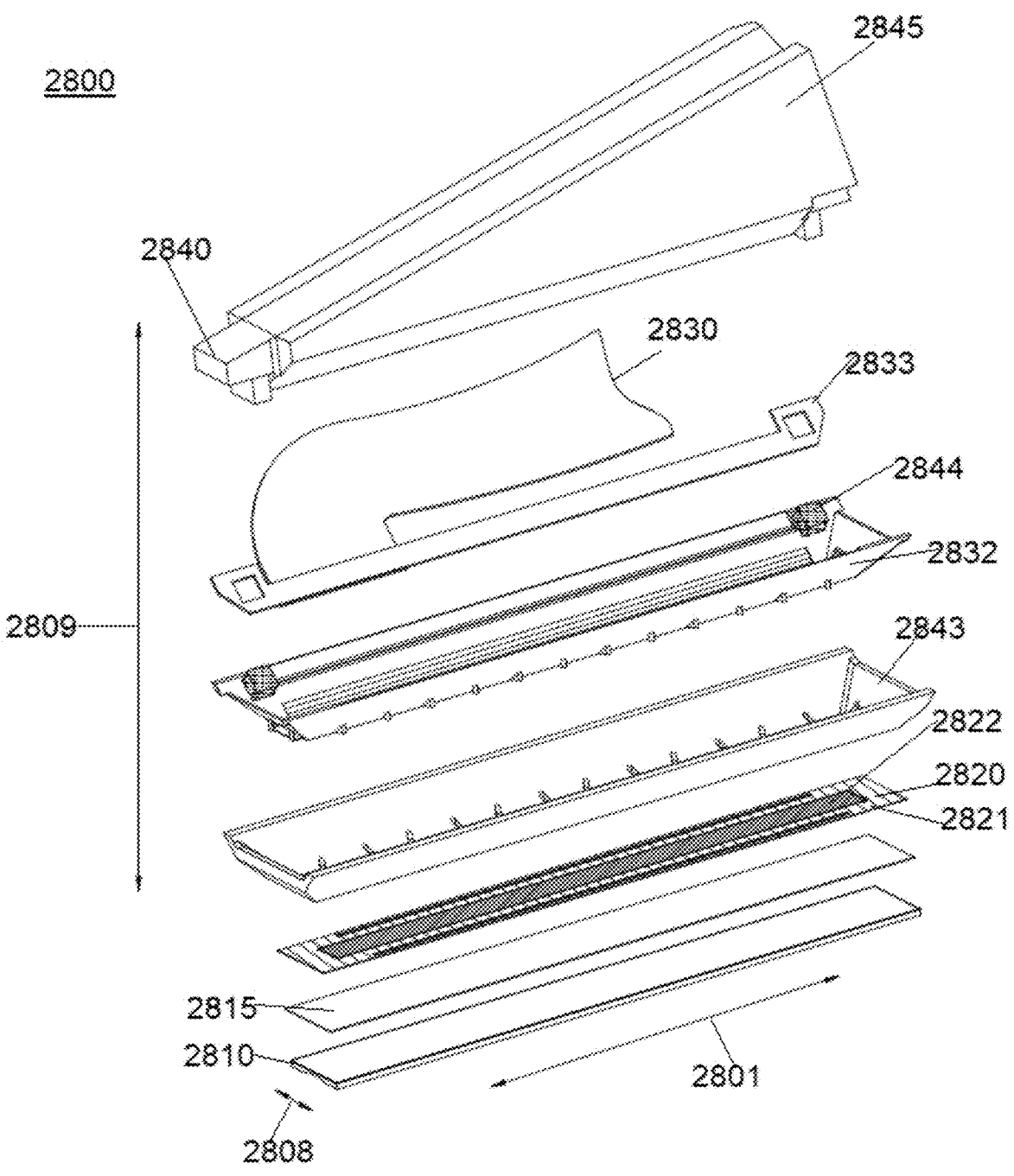
FIG. 28 depicts an exploded view of an example of a planar linear array stack for an ultrasound transducer.
Figure 29:
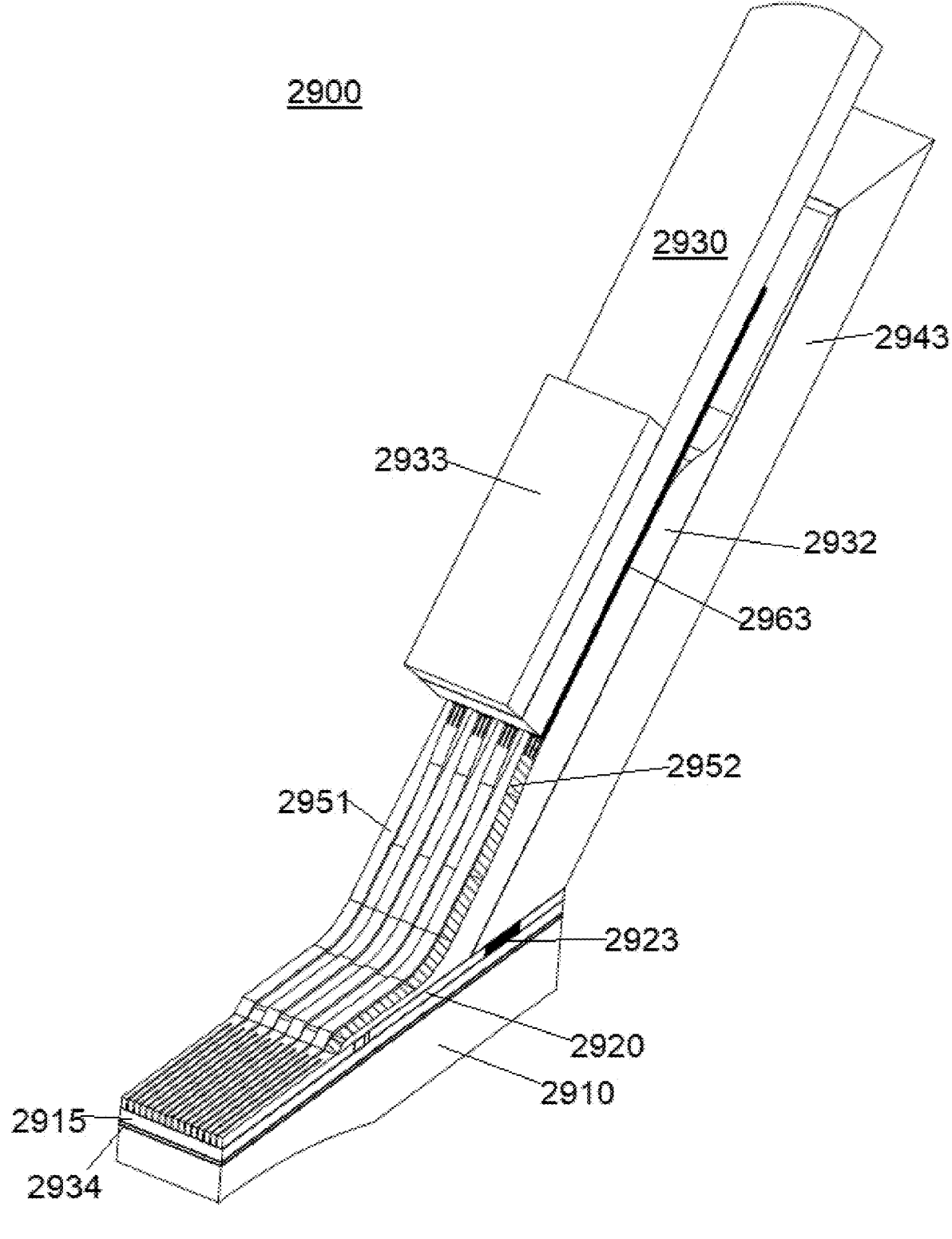
FIG. 29 provides an alternative view of the planar linear array of FIG. 28.
Figure 30:
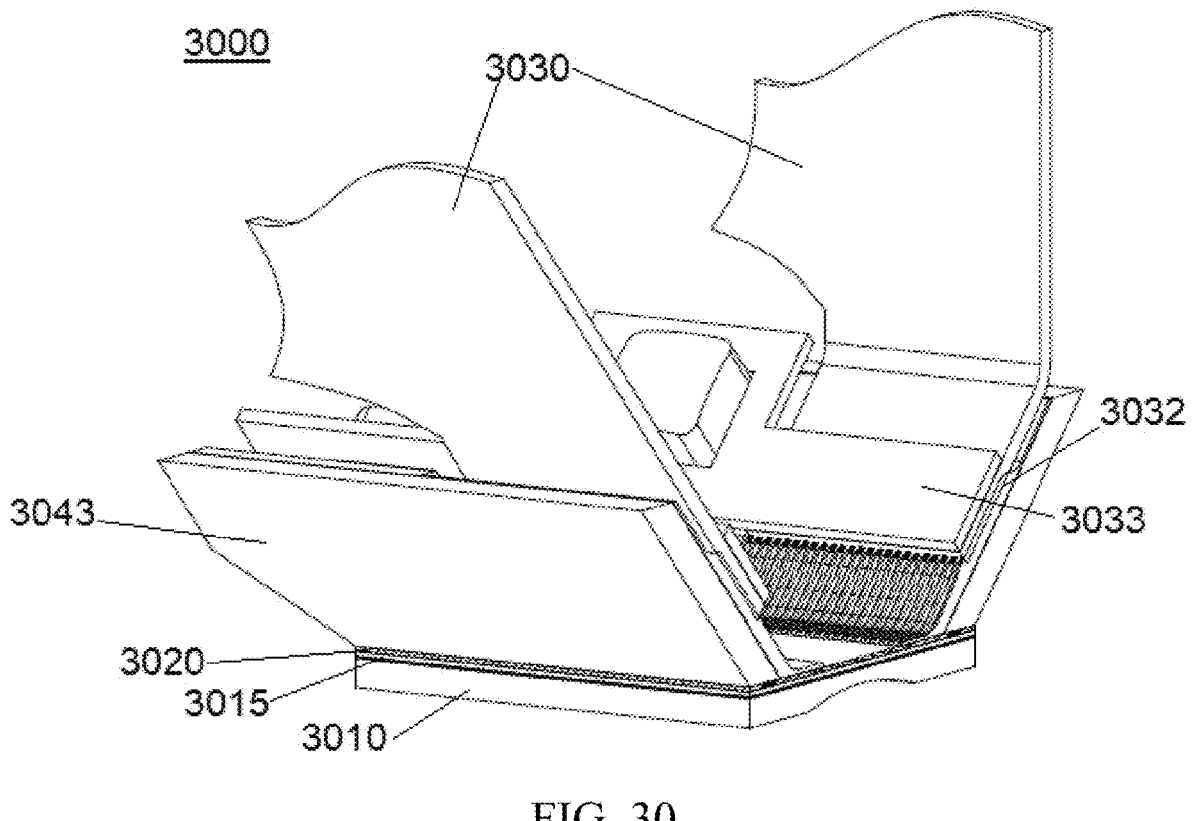
FIG. 30 illustrates a blown-up view of the planar linear array that includes a tapered structure.

FIGS. 28, 29, 30, and 31 illustrate the planar structure described herein but unlike some other examples, these examples include a tapered structure 2343 (e.g., FIG. 23), which can also be referred to and/or understood as a tapered support. This tapered structure 2343 (e.g., FIG. 23), is utilized in a planar structure in place of an interposer frame 125, 1225, 1325, 1425 (FIGS. 12, 13, and 14, respectively). In embodiments of the planar structure that include a tapered structure 2343 (e.g., FIG. 23), the overmould 932, 1032 (e.g., FIGS. 9 and 10) and one or more flex circuits 930 (FIG. 9), are bonded to the tapered structure 2343. These aspects are illustrated in FIGS. 28, 29, and 30.

To contrast this configuration with others described herein, FIG. 28 is similar to FIG. 1, but includes a tapered structure 2843 and excludes an interposer frame 125 (FIG. 1). FIG. 28 depicts an exploded view of an example of a planar linear array stack for an ultrasound transducer with a tapered structure 2843. FIG. 29 is similar to FIG. 10 in that it provides a view of various elements of the planar linear array stacks described herein, but this example includes a tapered structure 2943. FIG. 30, like FIG. 14, is a blown-up view of aspects of some planar linear array stacks described herein, but FIG. 30 includes a tapered structure 3043. Although the support is described herein as a tapered support, this descriptor is merely provided as an example as this structure can take various forms in different embodiments of the planar linear arrays for the transducers described herein.

FIG. 28 depicts an exploded view of an example of a planar linear array stack 2800 for an ultrasound transducer. In this figure, certain aspects are described in general terms and the figures that follow illustrate, in more detail, these aspects. The illustrated example of a planar linear array stack 2800 includes indicators of the width in longitudinal axis 2801, also referred to as longitudinal axis 2801, and the width axis 2808, and the stack-up thickness 2809. References herein to a bottom of the planar linear array stack 2800 refer to the planar linear array stack 2800 starting at the lens layer 2810. References herein to a top of the planar linear array stack 2800 refer to the planar linear array stack 2800 starting at the bending spacer 2845. Thus, like in the explanation of FIG. 1, in FIG. 28, when one describes a first element as being positioned below a second element, that means that the first element is closer to the lens layer 2810 than the second element. When one describes a first element as being above a second element, that means that the first element is closer to the bending spacer 2845 than the second element.

Referring to FIG. 28, planar linear array stack 2800 includes a lens layer 2810. This lens layer 2810 can include an acoustic lens secured to a lens support structure and the lens support structure or, in some examples, the lens layer 2810 can include an acoustic lens without a lens support structure. The acoustic lens utilized in various examples can be concave or convex. The acoustic lenses pictures in the figures herein are concave, by way of example, only.

The planar linear array stack 2800 also includes a piezoelectric layer 2820 including a piezoelectric material (e.g., PZT, PZT/SX, etc.) 2822. Although the piezoelectric material 2822 as well as the piezoelectric layer 2820 are illustrated as being rectangular, shapes can vary in various embodiments and the rectangular shape was selected for these examples for ease of illustration and not to suggest any limitations. Various embodiments of the present invention can include a piezoelectric material 2822 and a piezoelectric layer 2820 in various shapes, including but not limited to, rectangular, polygonal (e.g., including polygons that are not rectangular), ovaloid, ellipsoid, round, etc.

As will be illustrated in later figures this piezoelectric layer 2820 (e.g., FIG. 25, 2520) includes a non-metallic frame 2821 (e.g., FIG. 25, 2521) which is not comprised of metal (e.g., it can be made of ceramic) and referred to as a "non-metallic frame" herein. In some examples, the non-metallic frame 2821 surrounds the piezoelectric material 2822 (e.g., FIG. 25, 2522) on four sides. This non-metallic frame 2821 of the piezoelectric layer 2820 can position the piezoelectric material 2822 in a central position (or any other desired position, such as offset from the center position), relative to the longitudinal axis 2801 and the width axis 2808, in the planar linear array stack 2800. The non-metallic frame 2821 of the piezoelectric layer 2820 not only positions the piezoelectric material 2822 (e.g., PZT) relative to the width axis 2808 and longitudinal axis 2801 in the planar linear array stack, but the non-metallic frame 2821 can also define an elevational depth (e.g., in the stack-up thickness 2809 dimension).

In some examples, such as the planar linear array stack 2800 of FIG. 28, at least one matching layer 2815 separates the lens layer 2810 and the piezoelectric layer 2820. The matching layer 2815 can provide a material buffer from acoustic impedance between elements in a transducer, including insulation elements and those elements a signal will be travelling through. A surface of the piezoelectric material 2822 in the piezoelectric layer 2820 which is proximate to the at least one matching layer 2815 can comprise at least one electrode. The surface electrically couples the piezoelectric material 2822 and the at least one matching layer 2815. Above the piezoelectric layer 2820 is a tapered structure 2843 (e.g., FIG. 23, 2343) that helps to position one or more flex circuits 2830. In some examples, one bonds the one or more flex circuits 2830 to the tapered structure 2843.

For ease of illustration, FIG. 28 depicts only a single flex circuit 2830. As will be illustrated in later figures, multiple flex circuits can be used and these flex circuits can electrically couple the tapered structure 2843 to the piezoelectric layer 2820. The flex circuits 2830 can be additionally coupled to a ground electrode. A flex locator tab 2844 on the overmould 2832 participates in bonding the one or more flex circuits 2830 to the tapered structure 2843. The flex circuits 2830 includes flex registration strips 2833 (e.g., FIG. 8, 833). In some examples, each flex registration strip 2833 joins four flex circuits 2830. The flex registration strip 2833 can provide precision alignment to the array elements at a 90-micron pitch (e.g., a linear alignment). An overmould 2832 secures the flex circuits 2830 to the tapered structure 2843. The backing preform 2840 fits the planar structure and reduces material costs; the costs are saved because the backing preform is smaller in volume than alternative structural guides and is built to accommodate the planar structure on the planar linear array. The backing preform 2823 locates the bending spacer 2846 which is used to guide the one or more flex circuits 2830.

FIG. 29 provides an alternative view (when compared to FIG. 28) of various elements of the planar linear array stack described herein (where the planar stack includes a tapered structure 2843, 2943). These views are provided in advance of describing a structure utilized in some embodiments to transmit an electrical signal from a tapered structure 2943 to traces on a surface of the one or more flex circuits 2930 (flex registration strips 2933 are also depicted), conductive shapes of uniform scale (e.g., FIG. 10, 1050. The conductive shapes of uniform scale in FIG. 10, which are present in this example but not visible from the vantage point of FIG. 29, are illustrated herein as spheres, but the spheres are provided as a non-limiting example as the shapes can include pyramids, cubes, etc. The shapes comprising the conductive shapes of uniform scale in a planar linear array stack can be uniform or mixed, and they can be of uniform height along the stack up thickness 2809 axis (FIG. 28). The materials of the shapes and their alignment can vary in different examples and can include pure gold to Cu finger in direct contact (face to face), silver (which can improve the liability of electric contact rate), and/or Cu fingers on a flex facing up.

The planar linear array 2900, as depicted in FIG. 29 and moving upwards (e.g., FIG. 28), from the lens layer 2810 to the bending spacer 2845, along the stack up thickness 2809 axis), this array includes a lens layer 2910 that can include an acoustic lens with a curvature. Above the top surface of the lens layer 2910 is one or more matching layers 2915. A bonding agent, including but not limited to lens bonding glue 2934 bonds an upper surface of the lens layer 2910 to the piezoelectric layer 2920 and/or a matching layer 2915 to the piezoelectric layer 2920. The piezoelectric layer 2920 includes piezoelectric material 2822 (FIG. 28) and can include electrodes on both sides, a non-metallic frame 2821 (FIG. 28) and ground trenches 2923. The flex circuits 2930 can be connected to a ground electrode after they are bent. This connection is described and illustrated in greater detail in FIG. 9B.

A tapered structure 2943 is partially located on a horizontal plane above (relative to the stack up thickness 2809, FIG. 28) above the piezoelectric layer 2920. An overmould 2932 is on a surface that includes an upper surface of the tapered structure 2943. The overmould can comprise electrodes (e.g., gold, copper) on its upper surface. In the illustrated example, the upper surface of the overmould 2932 includes copper fingers 2963 as conductive shapes. As explained earlier, various examples herein can include a variety of different types of conductive shapes. As illustrated in FIG. 29, the overmould 2932 structure includes separation ridges 2951 and trenches 2952 that are lower than the separation ridges 2951. These trenches 2952 are coated with a conductive material, including but not limited to, gold. In some examples, the trenches 2952 are gold channels. The overmould 2932, and the one or more flex circuits 2930, are bonded to the tapered structure 2943.

FIG. 30 illustrates a blown-up view of the planar array 3000 that includes the tapered structure 3043. The overmould 3032, and the one or more flex circuits 3030, are bonded to the tapered structure 3043 and the flex registration strips 3033. To illustrate the orientation of the tapered structure 3043 within the array (e.g., FIG. 28, 2800), FIG. 30 illustrates elements described in other figures, such as the lens layer 2810, 2910, 3010, the overmould 2832, 2932, 3032, and the flex registration strips 2833, 2933, 3033. Also illustrated in FIG. 30 are a piezoelectric layer 3020 and a matching layer 3015.

Figure 31:
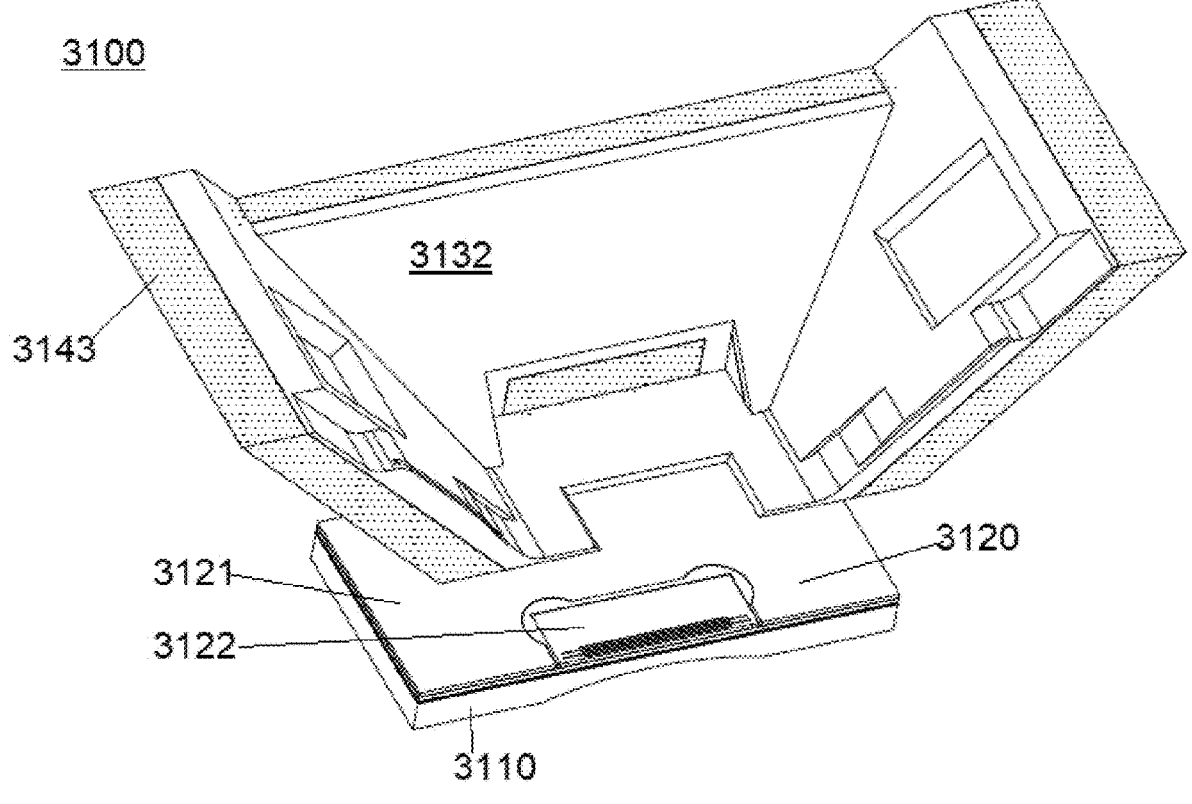
FIG. 31 illustrates a top view of aspects of the planar linear array of FIGS. 28-30.

FIG. 31 illustrates a top view of aspects of the planar array 3100 described herein. FIG. 31 depicts the tapered structure 2843, 2943, 3043, 3143 partially disconnected from (in a somewhat exploded view) from the piezoelectric layer 2820, 2920, 3020, 3120. The tapered structure 3143 is coupled to the overmould 3132. Also illustrated in FIG. 31 is the lens layer 2810, 2910, 3010, 3110, and the piezoelectric layer 2820, 2920, 3020, 3120, which is comprised of a non-metallic frame 2821, 3121 surrounding a piezoelectric material 2822, 3122 on four sides. Beneath the piezoelectric layer 3120 is the lens layer 3110.

Examples herein include piezoelectric layers of an ultrasound transducer, ultrasound transducers, methods of manufacturing the transducers, and methods of manufacturing the piezoelectric layers of an ultrasound transducer. In some examples of the piezoelectric layer of an ultrasound transducer, the piezoelectric layer comprises a non-metallic frame. In these examples, the piezoelectric layer also comprises a piezoelectric material. The non-metallic frame surrounds the piezoelectric material on at least two sides, the non-metallic frame is coupled to a lens support structure with a structure such that an acoustic lens and the piezoelectric material are oriented substantially parallel to each other. The piezoelectric material is sized to span an area greater than or equal to an active surface of the acoustic lens.

In some examples of the piezoelectric layer, the non-metallic frame comprises a ceramic.

In some examples of the piezoelectric layer, the non-metallic frame comprises at least one cutout in one or more of the at least two sides of the non-metallic frame, where the at least one cutout in the one or more of the at least two sides forms a portion of a ground path.

In some examples of the piezoelectric layer, the at least one cutout comprises a groove.

In some examples of the piezoelectric layer, the piezoelectric material comprises kerf cuts filled with a cured kerf fill material.

In some examples of the piezoelectric layer, the piezoelectric layer further comprises a sputtered metallic layer on a surface of the piezoelectric material.

In some examples of the piezoelectric layer, the at least two sides comprise four sides, and wherein the piezoelectric material is rectangular, trapezoid, ovaloid, ellipsoid, round, or square.

In some examples of the piezoelectric layer, the structure comprises a tapered structure.

In some examples, an ultrasound transducer comprises a planar linear array stack. In these examples, the planar linear array stack can include a lens layer comprising an acoustic lens and a lens support structure and a piezoelectric layer. The piezoelectric layer can include a non-metallic frame and a piezoelectric material. In some examples, the non-metallic frame surrounds the piezoelectric material on at least two sides. The non-metallic frame is coupled to the lens support structure with a structure such that a portion of the acoustic lens and a portion of the non-metallic frame are oriented substantially parallel to each other, the piezoelectric material sized to span an area greater than or equal to an active surface of the acoustic lens. The structure positions one or more flex circuits, where the one or more flex circuits are coupled to the structure.

In some examples of the ultrasound transducer, the lens support structure comprises a first bar and a second bar, where the first bar and the second bar are situated on opposing sides of the acoustic lens.

In some examples of the ultrasound transducer, the lens support structure comprises a frame that surrounds a perimeter of the acoustic lens.

In some examples of the ultrasound transducer, the lens support structure comprises ceramic.

In some examples of the ultrasound transducer, the acoustic lens comprises a curvature, where the curvature has an extremum on a line, the line parallel to the piezoelectric material in the planar linear array stack.

In some examples of the ultrasound transducer, the acoustic lens comprises a dielectric material.

In some examples of the ultrasound transducer, the structure comprises a tapered structure.

In some examples of the ultrasound transducer, the non-metallic frame surrounding the piezoelectric material is bonded to an outer boundary of the piezoelectric material with a bonding agent.

In some examples of the ultrasound transducer, the planar linear array stack includes one or more matching layers between the lens layer and the piezoelectric layer.

In some examples of the ultrasound transducer, the piezoelectric layer comprises electrodes on a surface proximate to the one or more matching layers.

In some examples of the ultrasound transducer, the planar linear array stack includes an overmould, where the overmould secures the one or more flex circuits to the structure.

In some examples of the ultrasound transducer, the planar linear array stack includes one or more flex registration strips attached to the one or more flex circuits, where at least one flex registration strip is positioned on the overmould by at least one flex locator tab.

some examples of the ultrasound transducer, the planar linear array stack includes a backing preform in contact with a portion of the one or more flex circuits.

In some examples of the ultrasound transducer, the backing preform is coated with a conductive tape.

In some examples of the ultrasound transducer, the planar linear array stack includes: a bending spacer. In these examples, the bending spacer is positioned above the backing preform such that a portion of each flex circuit is perpendicular to the piezoelectric layer of the planar linear array stack.

In some examples, an ultrasound transducer comprises a planar linear array stack. The planar linear array stack can include a lens layer comprising a lens, one or more matching layers between the lens layer and a piezoelectric layer, and a piezoelectric layer. The piezoelectric layer can include a non-metallic frame and a piezoelectric material. In these examples, the non-metallic frame surrounds the piezoelectric material on at least two sides, the non-metallic frame is coupled to a portion of the lens support structure with a structure such that an acoustic lens and the non-metallic frame are oriented substantially parallel to each other, and the piezoelectric material sized to span an area greater than or equal to an active surface of the acoustic lens. The structure can position one or more flex circuits, where the one or more flex circuits are coupled to the structure.

Examples of a method of manufacturing a piezoelectric layer of an ultrasound transducer can comprise dicing piezoelectric material to form a sized piece of piezoelectric material, the dicing including sizing the sized piece of piezoelectric material to span an area equivalent to an active surface of an acoustic lens in the ultrasound transducer. The method can include assembling a four-sided frame from a non-metallic material. The method can include forming at least one trench in at least one side of two parallel sides of the four-sided frame. The method can include bonding the sized piece of piezoelectric material to the four-sided frame such that the four-sided frame surrounds the sized piezoelectric material on at least two sides. The method can include cutting the sized piezoelectric material to form one or more kerfs oriented in a consistent direction. The method can include filling the kerfs with a material that cures over a time period. Based on the time period elapsing, the method can include sputtering at least the sized piece of piezoelectric material with a conductive material.

In some examples of the method, the method further comprises bonding the piezoelectric layer to a structure, where based on the bonding, the at least one trench in the at least one side of the two parallel sides forms a portion of a ground path with the structure.

In some examples of the method, the method further comprises lapping the sized piece of piezoelectric material before the kerf cutting.

In some examples of the method, the method further comprises lapping and cleaning each trench before the sputtering.

In some examples of the method, the conductive material is a metal.

In some examples of the method, the metal is selected from the group consisting of gold, silver, and copper.

In some examples of the method, the at least one trench is selected from the group consisting of: a cut-out, a channel, a hole, a groove, a slot, a canal, a corrugation, a creases, a crimp, and a cut.

In some examples of the method, the time period is less than or equal to one day.

In some examples of the method, the at least one trench, when the piezoelectric layer is implemented in an ultrasound transducer, participates in bringing ground connections from a front to a back of the piezoelectric layer to form part of a return signal path for the ultrasound transducer.

In some examples of the method, the lapping comprises parallel lapping.

Examples of a method of manufacturing a piezoelectric layer of an ultrasound transducer can comprise dicing piezoelectric material to form one or more sized pieces of piezoelectric material, where the dicing comprises sizing each piece of the one or more sized pieces of piezoelectric material to span at least an area of an active surface of an acoustic lens in an ultrasound transducer. The method can also include assembling one or more four-sided frames from a non-metallic material. The method can also include forming at least one trench in each side of two parallel sides of each frame of the one or more four-sided frames four-sided frames. The method can include stretching and placing foil over an object comprising a first parallel surface. The method can include placing a one or more stencils on a top surface of the foil, where each stencil of the one or more stencils comprises an opening to receive and retains in a set position, each sized piece of the one or more sized pieces. The method can include utilizing each stencil of the one or more stencils to position a respective sized piece of the one or more sized pieces. The method can include bonding each non-metallic frame of the one or more non-metallic frames to a respective sized piece of the one or more sized pieces. The method can include placing a second object comprising a second parallel surface, where the first parallel surface and the second parallel surface are parallel to each other, atop the one or more non-metallic frames.

In some examples, the method comprises removing the first object, the second object, the one or more stencils, and the foil to form the one or more piezoelectric layers.

In some examples, the bonding each non-metallic frame of the one or more non-metallic frames to the respective sized piece of the one or more sized pieces comprises positioning the respective sized piece such that the non-metallic frame surrounds the respective sized piece on at least two sides.

In some examples, each sized piece of the plurality of sized pieces is of a shape selected from the group consisting of: rectangle, ovaloid, round, non-rectangular polygon, and round.

In some examples, the removing is performed using a process selected from the group consisting of lapping, grinding, and milling.

In some examples, the method comprises for each piezoelectric layer of the one or more piezoelectric layers: kerf cutting the sized piezoelectric material to form one or more kerfs oriented in a consistent direction, filling the kerfs with a material that cures over a time period, and based on the time period elapsing, sputtering at least the sized piece of piezoelectric material with a conductive material.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description but is not intended to be exhaustive or limited to in the form disclosed. Many modifications and variations will be apparent to those of ordinary skill in the art. The embodiment was chosen and described to best explain various aspects and the practical application, and to enable others of ordinary skill in the art to understand various embodiments with various modifications as are suited to the particular use contemplated.

What is claimed is:

1. A piezoelectric layer of an ultrasound transducer, the piezoelectric layer comprising:
a non-metallic frame; and
a piezoelectric material, the non-metallic frame surrounding the piezoelectric material on at least two sides, the non-metallic frame coupled to a lens support structure with a first structure such that an acoustic lens and the piezoelectric material are oriented substantially parallel to each other, the piezoelectric material sized to span an area greater than or equal to an active surface of the acoustic lens,
wherein the non-metallic frame comprises at least one cutout in one or more of the at least two sides of the non-metallic frame, wherein the at least one cutout in the one or more of the at least two sides is filled with conductive material and forms a portion of a ground path.

2. The piezoelectric layer of claim 1, wherein the non-metallic frame comprises a ceramic.

3. The piezoelectric layer of claim 1, wherein the at least one cutout comprises a groove.

4. The piezoelectric layer of claim 1, wherein the piezoelectric material comprises kerf cuts filled with a cured kerf fill material.

5. The piezoelectric layer of claim 1, further comprising a sputtered metallic layer on a surface of the piezoelectric material.

6. The piezoelectric layer of claim 1, wherein the at least two sides comprise four sides, and wherein the piezoelectric material is rectangular, trapezoid, ovaloid, ellipsoid, round, or square.

7. The piezoelectric layer of claim 1, wherein the first structure comprises a tapered structure.

8. An ultrasound transducer, comprising:
a planar linear array stack, comprising:
a lens layer comprising an acoustic lens and a lens support structure; and
a piezoelectric layer comprising:
a non-metallic frame, wherein the non-metallic frame comprises at least one cutout in one or more of the at least two sides of the non-metallic frame, wherein the at least one cutout in the one or more of the at least two sides is filled with conductive material and forms a portion of a ground path;
a piezoelectric material, the non-metallic frame surrounding the piezoelectric material on at least two sides, the non-metallic frame coupled to the lens support structure with a first structure such that a portion of the acoustic lens and a portion of the non-metallic frame are oriented substantially parallel to each other, the piezoelectric material sized to span an area greater than or equal to an active surface of the acoustic lens; and
an overmould, and
the first structure to position one or more flex circuits, wherein the one or more flex circuits are coupled to the first structure, wherein the overmould is coupled between the one or more flex circuits and the piezoelectric material on a side of the piezoelectric material opposite the lens layer coupling to the piezoelectric layer, the overmould to secure the one or more flex circuits to the first structure.

9. The ultrasound transducer of claim 8, wherein the lens support structure comprises a first bar and a second bar, wherein the first bar and the second bar are situated on opposing sides of the acoustic lens.

10. The ultrasound transducer of claim 8, wherein the lens support structure comprises a frame that surrounds a perimeter of the acoustic lens.

11. The ultrasound transducer of claim 8, wherein the lens support structure comprises ceramic.

12. The ultrasound transducer of claim 8, wherein the acoustic lens comprises a curvature, wherein the curvature has an extremum on a line, the line parallel to the piezoelectric material in the planar linear array stack.

13. The ultrasound transducer of claim 8, wherein the acoustic lens comprises a dielectric material.

14. The ultrasound transducer of claim 8, wherein the first structure comprises a tapered structure.

15. The ultrasound transducer of claim 8, wherein the non-metallic frame surrounding the piezoelectric material is bonded to an outer boundary of the piezoelectric material with a bonding agent.

16. The ultrasound transducer of claim 15, wherein the planar linear array stack includes a backing preform in contact with a portion of the one or more flex circuits.

17. The ultrasound transducer of claim 16, wherein the backing preform is coated with a conductive tape.

18. The ultrasound transducer of claim 16, wherein the planar linear array stack includes:

a bending spacer, wherein the bending spacer is positioned above the backing preform such that a portion of each flex circuit is perpendicular to the piezoelectric layer of the planar linear array stack.

19. The ultrasound transducer of claim 8, wherein the planar linear array stack includes one or more matching layers between the lens layer and the piezoelectric layer.

20. The ultrasound transducer of claim 19, wherein the piezoelectric layer comprises electrodes on a surface proximate to the one or more matching layers.

21. The ultrasound transducer of claim 8, wherein the planar linear array stack includes one or more flex registration strips attached to the one or more flex circuits, wherein at least one flex registration strip is positioned on the overmould by at least one flex locator tab.

22. An ultrasound transducer, comprising:

a planar linear array stack, comprising:

a lens layer comprising a lens;

one or more matching layers between the lens layer and a piezoelectric layer; and a piezoelectric layer comprising:

a non-metallic frame; and a piezoelectric material, the non-metallic frame surrounding the piezoelectric material on at least two sides, the non-metallic frame coupled to a portion of the lens support structure with a first structure such that an acoustic lens and the non-metallic frame are oriented substantially parallel to each other, the piezoelectric material sized to span an area greater than or equal to an active surface of the acoustic lens, wherein the non-metallic frame comprises at least one cutout in one or more of the at least two sides of the non-metallic frame, wherein the at least one cutout in the one or more of the at least two sides is filled with conductive material and forms a portion of a ground path; and the first structure to position one or more flex circuits, wherein the one or more flex circuits are coupled to the structure.

* * * * *